United States Patent [19]

Shi et al.

[11] Patent Number: 6,046,035
[45] Date of Patent: Apr. 4, 2000

[54] POLYNUCLEOTIDES ENCODING A CARDIOTROPHIN-LIKE CYTOKINE

[75] Inventors: Yanggu Shi, Gaithersburg; Steven M. Ruben, Olney, both of Md.

[73] Assignee: Human Genome Sciences, Inc., Rockville, Md.

[21] Appl. No.: 09/106,182

[22] Filed: Jun. 29, 1998

Related U.S. Application Data

[60] Provisional application No. 60/051,311, Jun. 30, 1997.

[51] Int. Cl.[7] .............................. C12N 15/24; C07K 14/54
[52] U.S. Cl. .................... 435/69.52; 435/69.1; 536/23.5; 536/23.1; 530/351
[58] Field of Search ................................. 435/69.1, 69.4, 435/325, 320.1, 243, 69.52; 536/23.1, 23.572; 530/351

[56] References Cited

U.S. PATENT DOCUMENTS 5,741,772  4/1998  Chang .

FOREIGN PATENT DOCUMENTS 9833922  8/1998  WIPO .

OTHER PUBLICATIONS

Sheng et al., (1996) Development 122:419–428.

*Primary Examiner*—John Ulm
*Assistant Examiner*—Christine Saoud
*Attorney, Agent, or Firm*—Human Genome Sciences Inc.

[57] ABSTRACT

The present invention relates to a novel CLC protein which is a member of the IL-6 cytokine family. In particular, isolated nucleic acid molecules are provided encoding the human CLC protein. CLC polypeptides are also provided as are vectors, host cells and recombinant methods for producing the same. The invention further relates to screening methods for identifying agonists and antagonists of CLC activity. Also provided are diagnostic methods for detecting cardiac and immune system-related disorders and therapeutic methods for treating cardiac and immune system-related disorders.

5 Claims, 5 Drawing Sheets

Figure 1A
Cardiotrophin-like Cytokine

```
  1  GCCTCCGGGAGAGGAGCCGCACCCGGCCGGCCCGGCCCCAGCCCCATGGACCTCCGAGCA   60
  1                                                   M  D  L  R  A     5

61  GGGGACTCGTGGGGATGTTAGCGTGCCTGTGCACGGTGCTCTGGCACCTCCCTGCAGTG   120
  6  G  D  S  W  G  M  L  A  C  L  C  T  V  L  W  H  L  P  A  V       25

121  CCAGCTCTCAATCGCACAGGGGACCCAGGGCCTGGCCCCTCCATCCAGAAAACCTATGAC   180
 26  P  A  L  N  R  T  G  D  P  G  P  G  P  S  I  Q  K  T  Y  D       45

181  CTCACCCGCTACCTGGAGCACCAACTCCGCAGCTTGGCTGGGACCTATCTGAACTACCTG   240
 46  L  T  R  Y  L  E  H  Q  L  R  S  L  A  G  T  Y  L  N  Y  L       65

CD-I
241  GGCCCCCCTTTCAACGAGCCAGACTTCAACCCTCCCCGCCTGGGGGCAGAGACTCTGCCC   300
 66  G  P  P  F  N  E  P  D  F  N  P  P  R  L  G  A  E  T  L  P       85

301  AGGGCCACTGTTGACTTGGAGGTGTGGCGAAGCCTCAATGACAAACTGCGGCTGACCCAG   360
 86  R  A  T  V  D  L  E  V  W  R  S  L  N  D  K  L  R  L  T  Q      105

361  AACTACGAGGCCTACAGCCACCTTCTGTGTTACTTGCGTGGCCTCAACCGTCAGGCTGCC   420
106  N  Y  E  A  Y  S  H  L  L  C  Y  L  R  G  L  N  R  Q  A  A      125

421  ACTGCTGAGCTGCGCCGCAGCCTGGCCCACTTCTGCACCAGCCTCCAGGGCCTGCTGGGC   480
126  T  A  E  L  R  R  S  L  A  H  F  C  T  S  L  Q  G  L  L  G      145

CD-II
481  AGCATTGCGGGCGTCATGGCAGCTCTGGGCTACCCACTGCCCCAGCCGCTGCCTGGGACT   540
146  S  I  A  G  V  M  A  A  L  G  Y  P  L  P  Q  P  L  P  G  T      165

541  GAACCCACTTGGACTCCTGGCCCTGCCCACAGTGACTTCCTCCAGAAGATGGACGACTTC   600
166  E  P  T  W  T  P  G  P  A  H  S  D  F  L  Q  K  M  D  D  F      185

CD-III
601  TGGCTGCTGAAGGAGCTGCAGACCTGGCTGTGGCGCTCGGCCAAGGACTTCAACCGGCTC   660
186  W  L  L  K  E  L  Q  T  W  L  W  R  S  A  K  D  F  N  R  L      205

661  AAGAAGAAGATGCAGCCTCCAGCAGCTGCAGTCACCCTGCACCTGGGGGCTCATGGCTTC   720
206  K  K  K  M  Q  P  P  A  A  A  V  T  L  H  L  G  A  H  G  F      225

721  TGACTTCTGACCTTCTCCTCTTCGCTCCCCCTTCAAACCCTGCTCCCACTTTGTGAGAGC   780
225  *

781  CAGCCCTGTATGCCAACACCTGTTGAGCCAGGAGACAGAAGCTGTGAGCCTCTGGCCCTT   840
```

Figure 1B
Cardiotrophin-like Cytokine

```
 841   TCCTGGACCGGCTGGGCGTGTGATGCGATCAGCCCTGTCTCCTCCCCACCTCCCAAAGGT   900

901   CTACCGAGCTGGGGAGGAGGTACAGTAGGCCCTGTCCTGTCCTGTTTCTACAGGAAGTCA   960

961   TGCTCGAGGGAGTGTGAAGTGGTTCAGGTTGGTGCAGAGGCGCTCATGGCCTCCTGCTTC   1020

1021   TTGCCTACCACTTGGCCAGTGCCCACCCAGCCCCTCAGGTGGCACATCTGGAGGGCAGGG   1080

1081   GTTGAGGGGCCACCACCACACATGCCTTTCTGGGGTGAAGCCCTTTGGCTGCCCCACTCT   1140

1141   CCTTGGATGGGTGTTGCTCCCTTATCCCCAAATCACTCTATACATCCAATTCAGGAAACA   1200

1201   AACATGGTGGCAATTCTACACAAAAGAGATGAGATTAACAGTGCAGGGTTGGGGTCTGC   1260

1261   ATTGGAGGTGCCCTATAAACCAGAAGAGAAAATACTGAAAGCACAGGGGCAGGGACAGAC   1320

1321   CAGACCAGACCCAGGAGTCTCCAAAGCACAGAGTGGCAAACAAAACCCGAGCTGAGCATC   1380

1381   AGGACCTTGCCTCGAATTGTCTTCCAGTATTACGGTGCCTCTTCTCTGCCCCCTTTCCCA   1440

1441   GGGTATCTGTGGGTTGCCAGGCTGGGGAGGGCAACCATAGCCACACCACAGGATTTCCTG   1500

1501   AAAGTTTACAATGCAGTAGCATTTTGGGGTGTAGGGTGGCAGCTCCCCAAGGCCCTGCCC   1560

1561   CCCAGCCCCACCCACTCATGACTCTAAGTGTGTTGTATTAATATTTATTTATTTGGAGAT   1620

1621   GTTATTTATTAGATGATATTTATTGCAGAATTTCTATTCTTGTATTAACAAATAAAATGC   1680

1681   TTGCCCCAGAAAAAAAAAAAAAAAAAAAAA   1710
```

Figure 2
Cardiotrophin-like Cytokine

Percent Similarity: 47.849     Percent Identity: 29.032

HNFIR05
x
rat cardiotrophin

```
  2 DLRAGDSWGMLACLCTVLWHLPAVPALNRTGDPGPGPSIQKTYDLTRYLE 51
    |  ..:.|:::|: |                      ::.|..|.:|.|.|.
 10 DHQTDSSFSFLPHL.....................EAKIRQTHNLARLLT 38

52 HQLRSLAGTYLNYLGPPFNEPDFNPPRLGAETLPRATVDLEVWRSLNDKL 101
    .     | :.|:.   |.||. |:|.||||. ..|. :... .   :|  .
 39 KYADQLLEEYVQQQGEPFGLPGFSPPRLPLAGLSGPAPSHA...GLPVSE 85

102 RLTQNYEAYSHLLCYLRGLNRQAA.....TAELRRSLAHFCTSLQGLLGS 146
    || |: .|.| |  ..| ::.|..|      .: | |||.. .  :.:| :.
 86 RLRQDAAALSALPALLDAVRRRQAELNPRAPRLLRSLEDAARQVRALGAA 135

147 IAGVMAALGYPLPQPLP...GTEPTWTPGPAHSDFLQKMDDFWLLKELQT 193
    :..|:||||  : ..|:|    :|.: :|...|  : |  .|:  :: :    ...
136 VETVLAALGAAARGPVPEPVATSALFTSNSAAGVFSAKVLGLHVCGLYGE 185

194 WLWRSAKDFNRLKKKMQPPAAA 215
       |:.|..  |:...|    |.:.|
186 WVSRTEGDLGQL....VPGGVA 203
```

Figure 3
Cardiotrophin-like Cytokine Alignment

```
                    10            20            30
      1   M D L R - G D S W G M L A C L C T - V L W H L P A V P A L    HNFIR05.aa
      1   M S R R E - G S L E - - - - - - - - - - D P Q T D S S V    humCT1.aa
      1   M K V L A - A G V V P L L V L - - - - H W K H G A G S P L    LIF.aa
      1   M A F T E H S P L T P H R R D L C S R S I W - - - - - - -    CNTF.aa 40            50            60
     29   N R T G D P G P G P S I Q K T Y D - L T R Y L E H Q L R S L    HNFIR05.aa
     18   S L L P - H L E A K I R Q T - - H S L - - - - - A H L - - L    humCT1.aa
     26   P I T P V N A T C A I R H P C H N N L M N Q I R S Q L A Q L    LIF.aa
     23   - - - - - - - - - - - - - - - L A R K I R S D L T A L        CNTF.aa 70            80            90
     58   A G T - - - - - - - Y L N Y L G P P F N E P D F N P P R L G    HNFIR05.aa
     38   T K Y A E Q L L Q E Y V Q L Q G D P F G L P S F S P P R L P    humCT1.aa
     56   N G S A N A L F I L Y Y T A Q G E P F - - - P N N L D K L C    LIF.aa
     35   T E S - - - - - - - Y V K H Q G L - - - - - N K N I N L D S    CNTF.aa 100           110           120
     81   A E T L P R A T V D L E V W R S L N D K L R L T Q N Y E A Y    HNFIR05.aa
     68   V A G L S A P A P S H A - - - G L P V H E R L R L D A A A L    humCT1.aa
     83   G P N V T D F P P F H A - - - N G T E K A K L V E L Y R I V    LIF.aa
     53   A D G M P V A S T D Q - - W S E L T E A E R L Q E N L Q A Y    CNTF.aa 130           140           150
    111   S H L L C Y L R G L - N R Q A A - - - - - T A E L R R S L A    HNFIR05.aa
     95   A A L P P L L D A V - C R R Q A E L N P R A P R L L R R L E    humCT1.aa
    110   V Y L G T S L G N I - T R D Q K I L N P S A L S L H S K L N    LIF.aa
     81   R T F H V L L A R L L E D Q Q V H F T P T E G D F H Q A I H    CNTF.aa 160           170           180
    135   H F C T S L Q G L L G S I A G V M A A L G Y P L P Q P L P G    HNFIR05.aa
    124   D A A R Q A P A L G A A V E A L L A A L G A A N R G P R A E    humCT1.aa
    139   A T A D I L R G L - - - L S N V L C R L C S K Y H V G H V D    LIF.aa
    111   T L L L Q V A A F A Y Q I E E L M I L L E Y K I P R N E A D    CNTF.aa 190           200           210
    165   T E P T W T P G P A H S D - F L Q K M D D F W L L K E L Q T    HNFIR05.aa
    154   P P A A T A S A A S A T G V F P A K V L G L R V C G L Y R E    humCT1.aa
    166   - - V T Y G P D T S G K D V F Q K K K L G C Q L L G K Y K Q    LIF.aa
    141   G M P I - - - N V G D G G L F E K K L W G L K V L Q E L S Q    CNTF.aa 220           230           240
    194   W L W R S A K D F N R L K K K M Q P P A A A V T L H L G A H    HNFIR05.aa
    184   W L S R T E G D L G - - - - - - - - - - - - - - Q L L P G    humCT1.aa
    194   - - - - I I A V L A - - - - - - - - - - - - - - Q A F        LIF.aa
    168   W T V R S I H D L R F I S S H Q T G I P A R G S H Y I A N N    CNTF.aa 224   G F                                                         HNFIR05.aa
    199   G S A                                                       humCT1.aa
    202                                                               LIF.aa
    198   K K M                                                       CNTF.aa
```

Decoration 'Decoration #1': Shade (with solid black) residues that match the Consensus exactly.

Cardiotrophin-like Cytokine

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1710 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 46..720

(ix) FEATURE:
      (A) NAME/KEY: sig_peptide
      (B) LOCATION: 46..126

(ix) FEATURE:
      (A) NAME/KEY: mat_peptide
      (B) LOCATION: 127..720

(xi) SEQUENCE DESCRIPTION: SEQ ID NO:1:

```
GCCTCCGGGA GAGGAGCCGC ACCCGGCCGG CCCGGCCCCA GCCCC ATG GAC CTC            54
                                                 Met Asp Leu
                                                 -27     -25

CGA GCA GGG GAC TCG TGG GGG ATG TTA GCG TGC CTG TGC ACG GTG CTC         102
Arg Ala Gly Asp Ser Trp Gly Met Leu Ala Cys Leu Cys Thr Val Leu
            -20             -15                 -10

TGG CAC CTC CCT GCA GTG CCA GCT CTC AAT CGC ACA GGG GAC CCA GGG         150
Trp His Leu Pro Ala Val Pro Ala Leu Asn Arg Thr Gly Asp Pro Gly
        -5                   1               5

CCT GGC CCC TCC ATC CAG AAA ACC TAT GAC CTC ACC CGC TAC CTG GAG         198
Pro Gly Pro Ser Ile Gln Lys Thr Tyr Asp Leu Thr Arg Tyr Leu Glu
     10              15                  20

CAC CAA CTC CGC AGC TTG GCT GGG ACC TAT CTG AAC TAC CTG GGC CCC         246
His Gln Leu Arg Ser Leu Ala Gly Thr Tyr Leu Asn Tyr Leu Gly Pro
 25              30                  35                  40
```

```
CCT TTC AAC GAG CCA GAC TTC AAC CCT CCC CGC CTG GGG GCA GAG ACT         294
Pro Phe Asn Glu Pro Asp Phe Asn Pro Pro Arg Leu Gly Ala Glu Thr
                45                  50                  55

CTG CCC AGG GCC ACT GTT GAC TTG GAG GTG TGG CGA AGC CTC AAT GAC         342
Leu Pro Arg Ala Thr Val Asp Leu Glu Val Trp Arg Ser Leu Asn Asp
                60                  65                  70

AAA CTG CGG CTG ACC CAG AAC TAC GAG GCC TAC AGC CAC CTT CTG TGT         390
Lys Leu Arg Leu Thr Gln Asn Tyr Glu Ala Tyr Ser His Leu Leu Cys
            75                  80                  85

TAC TTG CGT GGC CTC AAC CGT CAG GCT GCC ACT GCT GAG CTG CGC CGC         438
Tyr Leu Arg Gly Leu Asn Arg Gln Ala Ala Thr Ala Glu Leu Arg Arg
            90                  95                  100

AGC CTG GCC CAC TTC TGC ACC AGC CTC CAG GGC CTG CTG GGC AGC ATT         486
Ser Leu Ala His Phe Cys Thr Ser Leu Gln Gly Leu Leu Gly Ser Ile
105                 110                 115                 120

GCG GGC GTC ATG GCA GCT CTG GGC TAC CCA CTG CCC CAG CCG CTG CCT         534
Ala Gly Val Met Ala Ala Leu Gly Tyr Pro Leu Pro Gln Pro Leu Pro
                125                 130                 135

GGG ACT GAA CCC ACT TGG ACT CCT GGC CCT GCC CAC AGT GAC TTC CTC         582
Gly Thr Glu Pro Thr Trp Thr Pro Gly Pro Ala His Ser Asp Phe Leu
                140                 145                 150

CAG AAG ATG GAC GAC TTC TGG CTG CTG AAG GAG CTG CAG ACC TGG CTG         630
Gln Lys Met Asp Asp Phe Trp Leu Leu Lys Glu Leu Gln Thr Trp Leu
                155                 160                 165

TGG CGC TCG GCC AAG GAC TTC AAC CGG CTC AAG AAG AAG ATG CAG CCT         678
Trp Arg Ser Ala Lys Asp Phe Asn Arg Leu Lys Lys Lys Met Gln Pro
                170                 175                 180

CCA GCA GCT GCA GTC ACC CTG CAC CTG GGG GCT CAT GGC TTC                 720
Pro Ala Ala Ala Val Thr Leu His Leu Gly Ala His Gly Phe
185                 190                 195

TGACTTCTGA CCTTCTCCTC TTCGCTCCCC CTTCAAACCC TGCTCCCACT TTGTGAGAGC       780

CAGCCCTGTA TGCCAACACC TGTTGAGCCA GGAGACAGAA GCTGTGAGCC TCTGGCCCTT       840

TCCTGGACCG GCTGGGCGTG TGATGCGATC AGCCCTGTCT CCTCCCCACC TCCCAAAGGT       900

CTACCGAGCT GGGGAGGAGG TACAGTAGGC CCTGTCCTGT CCTGTTTCTA CAGGAAGTCA       960

TGCTCGAGGG AGTGTGAAGT GGTTCAGGTT GGTGCAGAGG CGCTCATGGC CTCCTGCTTC      1020

TTGCCTACCA CTTGGCCAGT GCCCACCCAG CCCCTCAGGT GGCACATCTG GAGGGCAGGG      1080

GTTGAGGGGC CACCACCACA CATGCCTTTC TGGGGTGAAG CCCTTTGGCT GCCCCACTCT      1140

CCTTGGATGG GTGTTGCTCC CTTATCCCCA AATCACTCTA TACATCCAAT TCAGGAAACA      1200

AACATGGTGG CAATTCTACA CAAAAAGAGA TGAGATTAAC AGTGCAGGGT TGGGGTCTGC      1260

ATTGGAGGTG CCCTATAAAC CAGAAGAGAA AATACTGAAA GCACAGGGGC AGGGACAGAC      1320

CAGACCAGAC CCAGGAGTCT CCAAAGCACA GAGTGGCAAA CAAAACCCGA GCTGAGCATC      1380

AGGACCTTGC CTCGAATTGT CTTCCAGTAT TACGGTGCCT CTTCTCTGCC CCCTTTCCCA      1440

GGGTATCTGT GGGTTGCCAG GCTGGGGAGG GCAACCATAG CCACACCACA GGATTTCCTG      1500

AAAGTTTACA ATGCAGTAGC ATTTTGGGGT GTAGGGTGGG AGCTCCCCAA GGCCCTGCCC      1560

CCCAGCCCCA CCCACTCATG ACTCTAAGTG TGTTGTATTA ATATTTATTT ATTTGGAGAT      1620

GTTATTTATT AGATGATATT TATTGCAGAA TTTCTATTCT TGTATTAACA AATAAAATGC      1680

TTGCCCCAGA AAAAAAAAAA AAAAAAAAA                                       1710

(2) INFORMATION FOR SEQ ID NO:2:

(i) SEQUENCE CHARACTERISTICS:
```

(A) LENGTH: 225 amino acids
            (B) TYPE: amino acid
            (D) TOPOLOGY: linear (ii) MOLECULE TYPE: protein (xi) SEQUENCE DESCRIPTION: SEQ ID NO:2:

Met Asp Leu Arg Ala Gly Asp Ser Trp Gly Met Leu Ala Cys Leu Cys
-27     -25                 -20                 -15

Thr Val Leu Trp His Leu Pro Ala Val Pro Ala Leu Asn Arg Thr Gly
    -10             -5                  1               5

Asp Pro Gly Pro Gly Pro Ser Ile Gln Lys Thr Tyr Asp Leu Thr Arg
            10                  15                  20

Tyr Leu Glu His Gln Leu Arg Ser Leu Ala Gly Thr Tyr Leu Asn Tyr
            25                  30                  35

Leu Gly Pro Pro Phe Asn Glu Pro Asp Phe Asn Pro Arg Leu Gly
            40                  45                  50

Ala Glu Thr Leu Pro Arg Ala Thr Val Asp Leu Glu Val Trp Arg Ser
    55                  60                  65

Leu Asn Asp Lys Leu Arg Leu Thr Gln Asn Tyr Glu Ala Tyr Ser His
70                  75                  80                  85

Leu Leu Cys Tyr Leu Arg Gly Leu Asn Arg Gln Ala Ala Thr Ala Glu
            90                  95                  100

Leu Arg Arg Ser Leu Ala His Phe Cys Thr Ser Leu Gln Gly Leu Leu
            105                 110                 115

Gly Ser Ile Ala Gly Val Met Ala Ala Leu Gly Tyr Pro Leu Pro Gln
            120                 125                 130

Pro Leu Pro Gly Thr Glu Pro Thr Trp Thr Pro Gly Pro Ala His Ser
135                 140                 145

Asp Phe Leu Gln Lys Met Asp Asp Phe Trp Leu Leu Lys Glu Leu Gln
150             155                 160                 165

Thr Trp Leu Trp Arg Ser Ala Lys Asp Phe Asn Arg Leu Lys Lys Lys
            170                 175                 180

Met Gln Pro Pro Ala Ala Ala Val Thr Leu His Leu Gly Ala His Gly
            185                 190                 195

Phe (2) INFORMATION FOR SEQ ID NO:3:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Ser Gln Arg Glu Gly Ser Leu Glu Asp His Gln Thr Asp Ser Ser
1               5                   10                  15

Phe Ser Phe Leu Pro His Leu Glu Ala Lys Ile Arg Gln Thr His Asn
            20                  25                  30

Leu Ala Arg Leu Leu Thr Lys Tyr Ala Asp Gln Leu Leu Glu Glu Tyr
            35                  40                  45

Val Gln Gln Gln Gly Glu Pro Phe Gly Leu Pro Gly Phe Ser Pro Pro
        50                  55                  60

Arg Leu Pro Leu Ala Gly Leu Ser Gly Pro Ala Pro Ser His Ala Gly
65                  70                  75                  80

```
Leu Pro Val Ser Glu Arg Leu Arg Gln Asp Ala Ala Ala Leu Ser Ala
                85                  90                  95

Leu Pro Ala Leu Leu Asp Ala Val Arg Arg Gln Ala Glu Leu Asn
            100                 105                 110

Pro Arg Ala Pro Arg Leu Leu Arg Ser Leu Glu Asp Ala Ala Arg Gln
            115                 120                 125

Val Arg Ala Leu Gly Ala Ala Val Glu Thr Val Leu Ala Ala Leu Gly
        130                 135                 140

Ala Ala Ala Arg Gly Pro Val Pro Glu Pro Val Ala Thr Ser Ala Leu
145                 150                 155                 160

Phe Thr Ser Asn Ser Ala Ala Gly Val Phe Ser Ala Lys Val Leu Gly
                165                 170                 175

Leu His Val Cys Gly Leu Tyr Gly Glu Trp Val Ser Arg Thr Glu Gly
                180                 185                 190

Asp Leu Gly Gln Leu Val Pro Gly Gly Val Ala
                195                 200
```

(2) INFORMATION FOR SEQ ID NO:4:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ser Arg Arg Glu Gly Ser Leu Glu Asp Pro Gln Thr Asp Ser Ser
1               5                   10                  15

Val Ser Leu Leu Pro His Leu Glu Ala Lys Ile Arg Gln Thr His Ser
            20                  25                  30

Leu Ala His Leu Leu Thr Lys Tyr Ala Glu Gln Leu Leu Gln Glu Tyr
        35                  40                  45

Val Gln Leu Gln Gly Asp Pro Phe Gly Leu Pro Ser Phe Ser Pro Pro
50                  55                  60

Arg Leu Pro Val Ala Gly Leu Ser Ala Pro Ala Pro Ser His Ala Gly
65                  70                  75                  80

Leu Pro Val His Glu Arg Leu Arg Leu Asp Ala Ala Leu Ala Ala
                85                  90                  95

Leu Pro Pro Leu Leu Asp Ala Val Cys Arg Arg Gln Ala Glu Leu Asn
            100                 105                 110

Pro Arg Ala Pro Arg Leu Leu Arg Arg Leu Glu Asp Ala Ala Arg Gln
            115                 120                 125

Ala Arg Ala Leu Gly Ala Ala Val Glu Ala Leu Leu Ala Ala Leu Gly
        130                 135                 140

Ala Ala Asn Arg Gly Pro Arg Ala Glu Pro Pro Ala Ala Thr Ala Ser
145                 150                 155                 160

Ala Ala Ser Ala Thr Gly Val Phe Pro Ala Lys Val Leu Gly Leu Arg
                165                 170                 175

Val Cys Gly Leu Tyr Arg Glu Trp Leu Ser Arg Thr Glu Gly Asp Leu
                180                 185                 190

Gly Gln Leu Leu Pro Gly Gly Ser Ala
        195                 200
```

(2) INFORMATION FOR SEQ ID NO:5:

(i) SEQUENCE CHARACTERISTICS:
    (A) LENGTH: 202 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:5:

```
Met Lys Val Leu Ala Ala Gly Val Val Pro Leu Leu Val Leu His
1               5                  10                  15

Trp Lys His Gly Ala Gly Ser Pro Leu Pro Ile Thr Pro Val Asn Ala
                20                  25                  30

Thr Cys Ala Ile Arg His Pro Cys His Asn Asn Leu Met Asn Gln Ile
            35                  40                  45

Arg Ser Gln Leu Ala Gln Leu Asn Gly Ser Ala Asn Ala Leu Phe Ile
        50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
        195                 200
```

(2) INFORMATION FOR SEQ ID NO:6:

(i) SEQUENCE CHARACTERISTICS:
    (A) LENGTH: 200 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:6:

```
Met Ala Phe Thr Glu His Ser Pro Leu Thr Pro His Arg Arg Asp Leu
1               5                  10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
```

```
                          85                  90                  95
His Phe Thr Pro Thr Glu Gly Asp Phe His Gln Ala Ile His Thr Leu
                     100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
       130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
       195                 200
```

(2) INFORMATION FOR SEQ ID NO:7:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GGCACGAGGC AGCCTCCAGC AGCTGCAGTC ACCCTGCACC TGGGGGCTCA TGGCTTCTAA    60
CTTCTGACCT TCTCCTCTTC GCTCCCCCTT CAAACCCTGC TCCCACTTTG TGAGAGCCAG   120
CCCTGTATGC CAACACCTGT TGAGCCAGGA GACAGAAGCT GTGAGCCTCT GGCCCTTTCC   180
TGGACCGGCT GGGCGTGTNA TGCGATCAGC CCTGTTTCCT CCCCACCTCC CAAAGGTCTA   240
CCGAGCTGGG GAGGAGGTAC AGTAGGCCCT GTCCTGTCCT GTTTCTACAG GANGTCATGC   300
TCGAGNGGAG TGTGAAGTGG TTTCAGGTTG GTGCAGAGGC GCTCATGGCC TCCTTGTTTN   360
TTGGCTACCA NTTGGGNCAA TGNCCAACCA GCCCTT                             396
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CGCCCATGGC TCAATCGCAC AGGG                                           24
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CGCAAGCTTT CAGAAGCCAT GAGCCC                                         26
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CGCGGATCCA TGGACCTCCG AGCAGGG                                27
```

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CGCGGTACCT CAGAAGCCAT GAGCCC                                 26
```

(2) INFORMATION FOR SEQ ID NO:12:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GCCGGATCCG CCACCATGAA CTCCTTCTCC ACAAGCGCCT TCGGTCCAGT TGCCTTCTCC     60
CTGGGGCTGC TCCTGGTGTT GCCTGCTGCC TTCCCTGCCC CAGTATGGAC CTCCGAGCAG    120
GG                                                                  122
```

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GGCCGGGTAC CTCAGAAGCC ATGAGCCC                               28
```

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
CTAGCCGGAT CCGCCACCAT GGACCTCCGA GCAGGG                      36
```

(2) INFORMATION FOR SEQ ID NO:15:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: protein (xi) SEQUENCE DESCRIPTION: SEQ ID NO:15:

```
WSWS                                                                     4
```

(2) INFORMATION FOR SEQ ID NO:16:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GCGCCTCGAG ATTTCCCCGA AATCTAGATT TCCCCGAAAT GATTTCCCCG AAATGATTTC          60

CCCGAAATAT CTGCCATCTC AATTAG                                              86
```

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GCGGCAAGCT TTTTGCAAAG CCTAGGC                                             27
```

(2) INFORMATION FOR SEQ ID NO:18:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CTCGAGATTT CCCCGAAATC TAGATTTCCC CGAAATGATT TCCCCGAAAT GATTTCCCCG          60

AAATATCTGC CATCTCAATT AGTCAGCAAC CATAGTCCCG CCCCTAACTC CGCCCATCCC         120

GCCCCTAACT CCGCCCAGTT CCGCCCATTC TCCGCCCCAT GGCTGACTAA TTTTTTTTAT         180

TTATGCAGAG GCCGAGGCCG CCTCGGCCTC TGAGCTATTC CAGAAGTAGT GAGGAGGCTT         240

TTTTGGAGGC CTAGGCTTTT GCAAAAGCT T                                         271
```

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GCGCTCGAGG GATGACAGCG ATAGAACCCC GG                                32

(2) INFORMATION FOR SEQ ID NO:20:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

GCGAAGCTTC GCGACTCCCC GGATCCGCCT C                                 31

(2) INFORMATION FOR SEQ ID NO:21:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

GGGGACTTTC CC                                                      12

(2) INFORMATION FOR SEQ ID NO:22:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

GCGGCCTCGA GGGACTTTC CCGGGGACTT TCCGGGGACT TTCCGGGACT TTCCATCCTG    60

CCATCTCAAT TAG                                                     73

(2) INFORMATION FOR SEQ ID NO:23:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GCGGCAAGCT TTTTGCAAAG CCTAGGC                                      27

(2) INFORMATION FOR SEQ ID NO:24:

(i) SEQUENCE CHARACTERISTICS:
            (A) LENGTH: 256 base pairs
            (B) TYPE: nucleic acid
            (C) STRANDEDNESS: single
            (D) TOPOLOGY: linear (ii) MOLECULE TYPE: DNA (genomic)

-continued (xi) SEQUENCE DESCRIPTION: SEQ ID NO:24:

```
CTCGAGGGGA CTTTCCCGGG GACTTTCCGG GGACTTTCCG GGACTTTCCA TCTGCCATCT        60

CAATTAGTCA GCAACCATAG TCCCGCCCCT AACTCCGCCC ATCCCGCCCC TAACTCCGCC       120

CAGTTCCGCC CATTCTCCGC CCCATGGCTG ACTAATTTTT TTTATTTATG CAGAGGCCGA       180

GGCCGCCTCG GCCTCTGAGC TATTCCAGAA GTAGTGAGGA GGCTTTTTTG GAGGCCTAGG       240

CTTTTGCAAA AAGCTT                                                      256
```

POLYNUCLEOTIDES ENCODING A CARDIOTROPHIN-LIKE CYTOKINE

This application claims benefit under 35 U.S.C. § 119(e) of the filing date of U.S. Provisional Application Ser. No. 60/051,311, filed on Jun. 30, 1997, which is hereby incorporated by reference in its entirety.

FIELD OF THE INVENTION

The present invention relates to a novel human gene encoding a polypeptide which is a member of the cytokine family. More specifically, isolated nucleic acid molecules are provided encoding a human polypeptide named cardiotrophin-like cytokine, hereinafter referred to as "CLC". CLC polypeptides are also provided, as are vectors, host cells and recombinant methods for producing the same. Also provided are diagnostic methods for detecting disorders related to the immune and cardiac systems, and therapeutic methods for treating such disorders. The invention further relates to screening methods for identifying agonists and antagonists of CLC activity.

BACKGROUND OF THE INVENTION

Cardiotrophin-like cytokine (CLC) is a novel member of the interleukin (IL)-6 cytokine family. Currently, the IL-6 cytokine family consists of IL-6, IL-11, cardiotrophin (CT)-1, ciliary neurotrophic factor (CNTF), leukemia inhibitory factor (LIF), and oncostatin-M (OSM). Each of these factors can induce a wide variety of growth and differentiation activities through their interaction with receptors consisting, in part, of a common signaling subunit designated gp 130 (Kishimoto, T., et al., *Blood* 86:1243–1254; 1995). For high affinity receptor binding, IL-6 and IL-11 induce the homodimerization of gp 130. IL-6-binding then recruits a protein termed the IL-6 binding chain, or gp80, to the IL-6/receptor complex (Murakami, M., et al., *Science* 260:1808–1810; 1993). On the other hand, CT-1, LIF, and OSM induce gp130 heterodimerization with the 190 kDa low affinity LIF receptor b (also designated gp190; Davis, S., et al., *Science* 260:1805–1808; 1993; Gearing, D. P., et al., *EMBO J.* 10:2839–2848; 1991). CNTF-binding also involves the interaction of a third cellular protein, designated the a-CNTF receptor subunit, with the gp 130/gp 190 heterodimer (Davis, S., et al., *Science* 253:59–63; 1991). Additional receptor binding subunits have also been identified in the cases of IL-11(Hilton, D. J., et al., *EMBO J.* 13:4765–4775; 1994) and OSM (Thoma, B., et al., *J. Biol. Chem.* 269:6215–6222; 1994), thus promoting an interest in the continued characterization of the interactions of IL-6 cytokine family members with their respective receptor complexes. In any case, induction of gp 130 receptor complex formation by IL-6 cytokine family member binding is followed by the activation of one or more cellular signal transduction pathways especially including the Jak/STAT pathway (Darnell, J. E., et al., *Science* 264:1415–1421; 1994).

The members of the IL-6 family exhibit many shared biological activities including the activation of hepatocellular transcription, the activation of neural cell proliferation and differentiation, and the regulation of hematopoiesis (Baumann, H., et al., *J. Biol. Chem.* 268:8414–8417; 1993; Yamamori, T., et al., *Science* 246:1412–1416; 1989; Leary, A. G., et al., *Blood* 75:1960–1964; 1990). Furthermore, CT-1, LIF, CNTF, and OSM have been detected in the early stages of development and also appear to allow embryonic stem cells to grow in an undifferentiated state in vitro (Smith, A. G., et al., *Nature* 336:688–690; 1988; Conover, J. C., et al., *Development* 119:559–565; 1993; Pennica, D., et al., *J. Biol. Chem.* 270:10915–10922; 1995).

A number of specific functions have also been ascribed to various members of the IL-6 cytokine family in addition to the common activities listed above. For example, OSM inhibits the growth of A375 human histiocytic melanoma cells and several types of lung, breast, ovary, and stomach tumor cell lines (Zarling, J. M., et al., *Proc. Natl. Acad. Sci. USA* 83:9739–9743; 1986; Brown, T. J., et al., *J. Immunol.* 139:2977–2983; 1987; Malik, N., et al., *Mol. Cell. Biol.* 9:2847–2853; 1989; Horn, D., et al., *Growth Factors* 2:157–165; 1990). Furthermore, OSM stimulates the growth of normal fibroblast cell lines, rabbit vascular smooth cells, bovine aortic endothelial cells, and Kaposi's sarcoma-derived spindle cells (Grove, R. I., et al., *Proc. Natl., Acad. Sci. USA* 90:823–827; 1993; Nair, B. C., et al., *Science* 255:1430–1432; 1992; Radka, S. F., et al., *J. Immunol.* 150:5195–5201; 1993).

Cardiotrophin-1, or CT-1, is the member of the IL-6 cytokine family most closely related by sequence identity to the amino acid sequence of the gene of the present invention. CT-1 was identified by combining an expression cloning approach with an embryonic stem cell-based model of in vitro cardiogenesis (Sheng, Z., et al., *Development* 122:419–428; 1996; Pennica, D., et al., *Proc. Natl. Acad. Sci. USA* 92:1142–1146; 1995; Ishikawa, M., et al., *Biochim. Biophys. Res. Comm.* 219:377–381; 1996). Adult cardiac muscle is terminally differentiated and, unlike skeletal muscle, cardiac muscle tissue does not contain muscle cells which retain their proliferative capacity. As a result, injury to the heart muscle is often irreversible and results in scarring and ultimately in an overall decrease in heart function.

In response to mechanical stimuli and hemodynamic stress, the adult myocardium can activate an "adaptive hypertrophic response" characterized by an increase in myocardial cell size, but not in cell number (Chien, K. R., et al., *Annu. Rev. Physiol.* 55:77–95; 1993). The specific type of hypertrophic response can be modulated by mechanical induction of an excess of pressure or an excess of volume on the cardiac system. During extended periods of hypertension (that is, excessive pressure on the system), a distinct form of myocardial cell hypertrophy can result in which individual cardiac myocytes increase in length, but not in diameter (Anversa, P., et al., *Circ. Res.* 52:57–64; 1983; Gerdes, A. M., et al., *Lab. Invest.* 59:857–861; 1988). The overall effect of excessive volume hypertrophy can be scarring, fibrosis, and the loss of viable cardiac myocytes throughout the heart, and, ultimately, an irreversible loss of heart function (Wollert, K. C., et al., *J. Biol. Chem.* 271:9535–9545; 1996), while the overall effect of pressure hypertrophy is usually characterized by a preservation of contractile function and is often reversible.

CT-1 was isolated in an attempt to identify factors which are involved in the above-described process of excessive volume-mediated myocardial cell hypertrophy. In addition, it has been observed that CT-1 can promote the survival of ventricular muscle cells in vitro (Sheng, Z., et al., *Development* 122:419–428; 1996). Currently, it is hypothesized that CT-1 may affect a survival phenotype on such muscle cells in culture in vitro through a mechanism in which CT-1 activates cellular signal transduction pathways which can block apoptosis of cardiac myocytes.

Thus, there is a need for polypeptides that function as mediators of cardiac hypertrophy, since disturbances of such regulation may be involved in disorders relating to the heart including arrhythmia, inotropia, heart failure, cardiomyophathy, hypertrophy, ischemia, hypertension, valvular or pericardial abnormalities. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the CLC polypeptide having the complete amino acid sequence shown in SEQ ID NO:2 or the complete amino acid sequence encoded by the cDNA clone designated HNFIR05 and deposited as plasmid DNA as ATCC Deposit Number 209122 on Jun. 19, 1997 [the ATCC Deposit Receipt designates the clone as having the following identification reference by depositor: "DNA Plasmid HNFIR05 (PF383)"]. The nucleotide sequence determined by sequencing the deposited CLC clone, which is shown in FIGS. 1A and 1B (SEQ ID NO:1), contains an open reading frame encoding a complete polypeptide of 225 amino acid residues, including an initiation codon encoding an N-terminal methionine at nucleotide positions 46–48, and a predicted molecular weight of about 25.2 kDa. Nucleic acid molecules of the invention include those encoding the complete amino acid sequence and the complete amino acid sequence excepting the N-terminal methionine shown in SEQ ID NO:2, or the complete amino acid sequence and the complete amino acid sequence excepting the N-terminal methionine encoded by the cDNA clone in ATCC Deposit Number 209122, which molecules also can encode additional amino acids fused to the N- or C-termini of the CLC amino acid sequence.

The encoded polypeptide has a predicted leader sequence of 27 amino acids underlined in FIG. 1A; and the amino acid sequence of the predicted mature CLC protein is also shown in FIGS. 1A and 1B, as amino acid residues 28–225 and as residues 1–198 in SEQ ID NO:2.

Thus, one aspect of the invention provides an isolated nucleic acid molecule comprising a polynucleotide comprising a nucleotide sequence selected from the group consisting of: (a) a nucleotide sequence encoding the CLC polypeptide having the complete amino acid sequence in SEQ ID NO:2 (i.e., positions –27 to 198 of SEQ ID NO:2); (b) a nucleotide sequence encoding the CLC polypeptide having the complete amino acid sequence in SEQ ID NO:2 excepting the N-terminal methionine (i.e., positions –26 to 198 of SEQ ID NO:2); (c) a nucleotide sequence encoding the predicted mature CLC polypeptide having the amino acid sequence at positions 1 to 198 in SEQ ID NO:2; (d) a nucleotide sequence encoding the CLC polypeptide having the complete amino acid sequence encoded by the cDNA clone contained in ATCC Deposit No. 209122; (e) a nucleotide sequence encoding the CLC polypeptide having the complete amino acid sequence excepting the N-terminal methionine encoded by the cDNA clone contained in ATCC Deposit No. 209122; (f) a nucleotide sequence encoding the mature CLC polypeptide having the amino acid sequence encoded by the cDNA clone contained in ATCC Deposit No. 209122; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical to (that is, at most 10% different from), and more preferably at least 95%, 96%, 97%, 98% or 99% identical to (or more preferably at most 5%, 4%, 3%, 2% or 1% different from), any of the nucleotide sequences in (a), (b), (c), (d), (e), (f) or (g) above, or a polynucleotide which hybridizes under stringent hybridization conditions to a polynucleotide in (a), (b), (c), (d), (e) or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CLC polypeptide having an amino acid sequence in (a), (b), (c), (d), (e) or (f) above.

The present invention also relates to recombinant vectors, which include the isolated nucleic acid molecules of the present invention, and to host cells containing the recombinant vectors, as well as to methods of making such vectors and host cells and for using them for production of CLC polypeptides or peptides by recombinant techniques.

The invention further provides an isolated CLC polypeptide comprising an amino acid sequence selected from the group consisting of: (a) the amino acid sequence of the full-length CLC polypeptide having the complete amino acid sequence shown in SEQ ID NO:2 (i.e., positions –27 to 198 of SEQ ID NO:2); (b) the amino acid sequence of the full-length CLC polypeptide having the complete amino acid sequence shown in SEQ ID NO:2 excepting the N-terminal methionine (i.e., positions –26 to 198 of SEQ ID NO:2); (c) the amino acid sequence of the mature CLC polypeptide having the complete amino acid sequence shown in SEQ ID NO:2 (i.e., positions 1 to 198 of SEQ ID NO:2); (d) the amino acid sequence of the full-length CLC polypeptide =encoded by the cDNA clone contained in ATCC Deposit No. 209122; (e) the amino acid sequence of the full-length CLC polypeptide having the complete amino acid sequence, excepting the N-terminal methionine, encoded by the cDNA clone contained in ATCC Deposit No. 209122, and; (f) the amino acid sequence of the full-length CLC polypeptide having the complete amino acid sequence, excepting the N-terminal methionine, encoded by the cDNA clone contained in ATCC Deposit No. 209122. The polypeptides of the present invention also include polypeptides having an amino acid sequence at least 80% identical to (or at most 20% different from), more preferably at least 90% identical to (that is, at most 10% different from), and still more preferably 95%, 96%, 97%, 98% or 99% identical to (or at most 5%, 4%, 3%, 2% or 1% different from) those described in (a), (b), (c), (d), (e), or (f) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a CLC polypeptide having an amino acid sequence described in (a), (b), (c), (d), (e) or (f), above. Peptides or polypeptides having the amino acid sequence of an epitope-bearing portion of a CLC polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a CLC polypeptide having an amino acid sequence described in (a), (b), (c), (d), (e) or (f), above. The invention further provides methods for isolating antibodies that bind specifically to a CLC polypeptide having an amino acid sequence as described herein. Such antibodies are useful diagnostically or therapeutically as described below.

The invention also provides for pharmaceutical compositions comprising CLC polypeptides, particularly human CLC polypeptides, which may be employed, for instance, to treat disorders relating to the heart including arrhythmia, inotropia, heart failure, cardiomyophathy, hypertrophy, ischemia, hypertension, valvular or pericardial abnormalities. Methods of treating individuals in need of CLC polypeptides are also provided.

The invention further provides compositions comprising a CLC polynucleotide or an CLC polypeptide for administration to cells in vitro, to cells ex vivo and to cells in vivo, or to a multicellular organism. In certain particularly preferred embodiments of this aspect of the invention, the compositions comprise a CLC polynucleotide for expression of a CLC polypeptide in a host organism for treatment of disease. Particularly preferred in this regard is expression in a human patient for treatment of a dysfunction associated with aberrant endogenous activity of a CLC.

The present invention also provides a screening method for identifying compounds capable of enhancing or inhibiting a biological activity of the CLC polypeptide, which involves contacting a receptor which is inhibited or enhanced by the CLC polypeptide with the candidate compound in the presence of a CLC polypeptide, assaying the stimulation of an appropriate signal transduction cascade of the receptor in the presence of the candidate compound and of CLC polypeptide, and comparing the receptor activity to a standard level of activity, the standard being assayed when contact is made between the receptor and in the presence of the CLC polypeptide and the absence of the candidate compound In this assay, an increase in receptor activity over the standard indicates that the candidate compound is an agonist of CLC activity and a decrease in receptor activity compared to the standard indicates that the compound is an antagonist of CLC activity.

It has been discovered that CLC is expressed not only in activated human neutrophils, but also in bone marrow stromal cells, synovial fibroblasts, peripheral blood mononuclear cells, ovarian tumor cells, spleen, testis, and leukocytes. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the cardiac and immune systems, significantly higher or lower levels of CLC gene expression may be detected in certain tissues (e.g., cancerous and wounded tissues) or bodily fluids (e.g., serum, plasma, urine, synovial fluid or spinal fluid) taken from an individual having such a disorder, relative to a "standard" CLC gene expression level, i.e., the CLC expression level in healthy tissue from an individual not having the cardiac or immune system disorder. Thus, the invention provides a diagnostic method useful during diagnosis of such a disorder, which involves: (a) assaying CLC gene expression level in cells or body fluid of an individual; (b) comparing the CLC gene expression level with a standard CLC gene expression level, whereby an increase or decrease in the assayed CLC gene expression level compared to the standard expression level is indicative of disorder in the cardiac or immune systems.

An additional aspect of the invention is related to a method for treating an individual in need of an increased level of CLC activity in the body comprising administering to such an individual a composition comprising a therapeutically effective amount of an isolated CLC polypeptide of the invention or an agonist thereof.

A still further aspect of the invention is related to a method for treating an individual in need of a decreased level of CLC activity in the body comprising administering to such an individual a composition comprising a therapeutically effective amount of an CLC antagonist. Preferred antagonists for use in the present invention are CLC-specific antibodies.

BRIEF DESCRIPTION OF THE FIGURES

FIGS. 1A and 1B show the nucleotide sequence (SEQ ID NO:1) and deduced amino acid sequence (SEQ ID NO:2) of CLC. The predicted leader sequence of about 27 amino acids is underlined. Note that the methionine residue at the beginning of the leader sequence in FIG. 1A is shown in position number +1, whereas the leader positions in the corresponding sequence of SEQ ID NO:2 are designated with negative position numbers. Thus, the leader sequence positions 1 to 27 in FIG. 1A correspond to positions −27 to −1 in SEQ ID NO:2. An asparagine (N) residue at position 29 of the CLC amino acid sequence shown in FIG. 1A (position +2 in SEQ ID NO:2) which is a component of an N-linked glycosylation consensus sequence. As such, this asparagine residue may potentially be involved in an N-linked glycosylation event and is delineated with a bolded pound sign (#) above the first nucleotide encoding the residue and a bolded asparagine symbol (N) in the CLC amino acid sequence in FIG. 1A.

Figure 4:
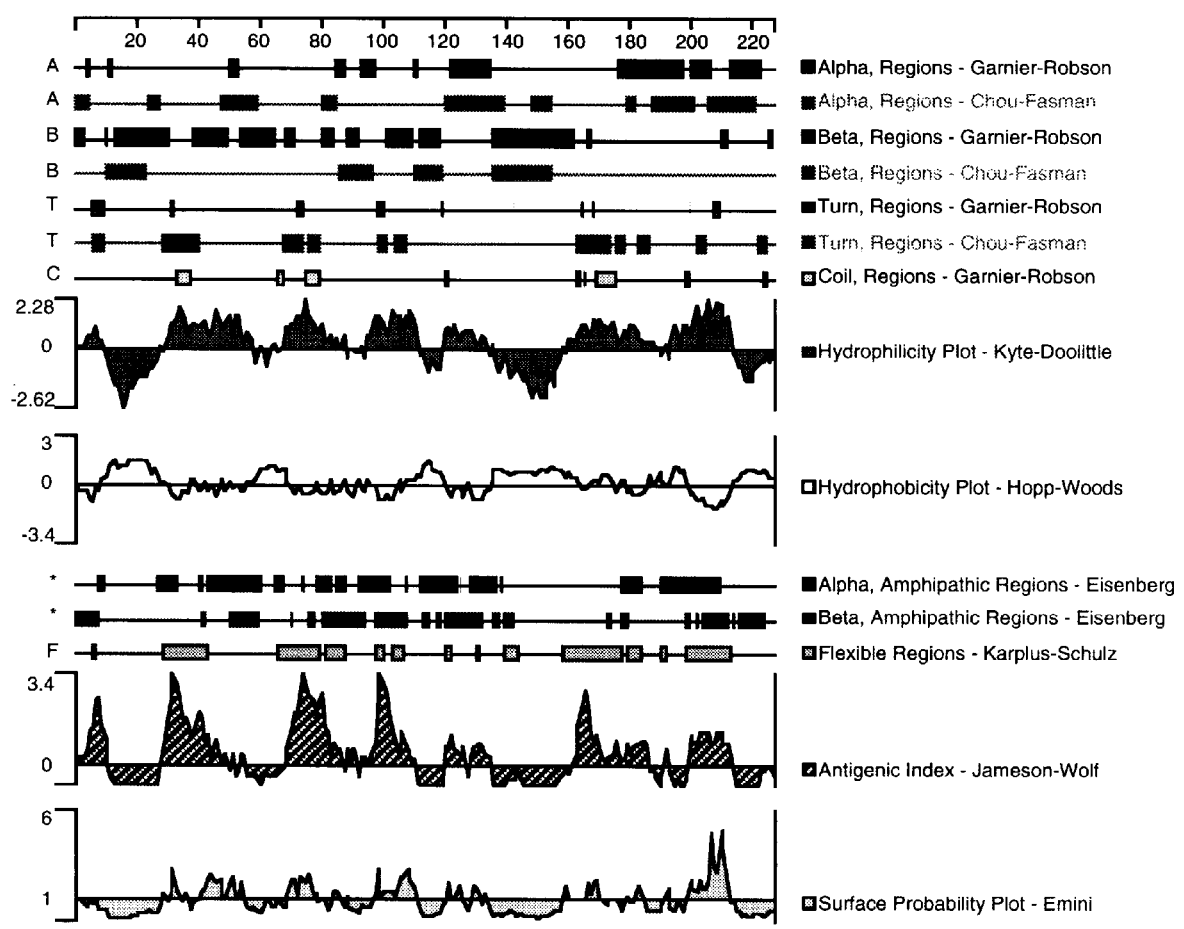

Three regions of the CLC amino acid sequence which appear to be highly conserved with regard to human cardiotrophin, LIF, and CNTF (see FIG. 3) are indicated by a double underline and are labeled as conserved domain (CD)-I, CD-II, and CD-III in FIG. 1A.

FIG. 2 shows the regions of identity between the amino acid sequences of the CLC protein and translation product of the rat cardiotrophin-1 MRNA (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows the regions of identity between the amino acid sequences of the CLC protein, human cardiotrophin (SEQ ID NO:4), LIF (SEQ ID NO:5), and CNTF (SEQ ID NO:6) mRNA, determined by the computer program MegAlign (DNASTAR, Inc.) using the default parameters. In the figure, the amino acid sequences of CLC, human cardiotrophin, LIF, and CNTF are labeled as HNFIR05.aa, humCT1.aa, LIF.aa, and CNTF.aa, respectively.

FIG. 4 shows an analysis of the CLC amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the CLC protein, i.e., regions from which epitope-bearing peptides of the invention can be obtained.

DETAILED DESCRIPTION

The present invention provides isolated nucleic acid molecules comprising a polynucleotide encoding a CLC polypeptide having the amino acid sequence shown in SEQ ID NO:2, which was determined by sequencing a cloned cDNA. The nucleotide sequence shown in FIGS. 1A and 1B (SEQ ID NO:1) was obtained by sequencing the HNFIR05 clone, which was deposited on Jun. 19, 1997 at the American Type Culture Collection (ATCC), 10801 University Blvd., Manassas, Va. 20110-2209, and given accession number ATCC 209122. The deposited clone is contained in the pBluescript SK(-) plasmid (Stratagene, La Jolla, Calif.).

The CLC protein of the present invention shares sequence homology with the translation product of the rat cardiotrophin-1 (FIG. 2; SEQ ID NO:3), human cardiotrophin, LIF, and CNTF mRNAs (FIG. 3; SEQ ID NO:4, SEQ ID NO:5, and SEQ ID NO:6, respectively). Cardiotrophin is thought to be an important regulator of cardiac muscle hypertrophy. As detailed in the background section, cardiotrophin, or CT-1, was identified as a factor which is involved in the process of excessive volume-mediated myocardial cell hypertrophy. Cardiac cell hypertrophy due to excessive volume can result in scarring, fibrosis, and the loss of viable cardiac myocytes throughout the heart, and, ultimately, an irreversible loss of heart function, while cardiac cell hypertrophy due to excessive pressure is usually characterized by a preservation of contractile function and is often reversible. In addition, it has been observed that CT-1 can promote the survival of ventricular muscle cells in vitro and it is hypothesized that CT-1 may affect a survival phenotype on such muscle cells in culture in vitro through a mechanism in which CT-1 activates cellular signal transduction pathways which can block apoptosis of cardiac myocytes.

LIF and CNTF share sequence relatedness with both CT-1 and CLC. LIF and CNTF are two additional members of the haematopoietic and neurotrophic cytokine family of IL-6-like factors. The entire family of IL-6-like cytokines exhibit overlapping biological activities and are known to function in the neuronal system. LIF exhibits proliferative, survival and differentiation activities on a wide range of cell types. In addition, a role for LIF in embryonic development is evidenced by its ability to stimulate the proliferation of embryonic stem cells in vitro, and its embryonic expression pattern at the time of blastocyst implantation.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A and 1B (SEQ ID NO:1), a nucleic acid molecule of the present invention encoding a CLC polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from activated neutrophils. Additional clones of the same gene were also identified in cDNA libraries from the following cells and/or tissues: bone marrow stromal cells, synovial fibroblasts, peripheral blood mononuclear cells, and ovarian tumor cells.

The determined nucleotide sequence of the CLC cDNA of FIGS. 1A and 1B (SEQ ID NO:1) contains an open reading frame encoding a protein of 225 amino acid residues, with an initiation codon at nucleotide positions 46–48 of the nucleotide sequence in FIG. 1A (SEQ ID NO:1), and a deduced molecular weight of about 25.2 kDa. The amino acid sequence of the CLC protein shown in SEQ ID NO:2 is about 29.0% identical and 47.8% similar to rat cardiotrophin-1 mRNA (FIG. 2; Ishikawa, M., et al., *Biochem. Biophys. Res. Commun.* 219:377–381; 1996; GenBank Accession No. D7859 1). The homology between CT-1 and CLC indicates that CLC may be involved in similar physiological roles.

As one of ordinary skill would appreciate, due to the possibilities of sequencing errors discussed above, the actual complete CLC polypeptide encoded by the deposited cDNA, which comprises about 225 amino acids, may be somewhat longer or shorter. More generally, the actual open reading frame may be anywhere in the range of ±20 amino acids, more likely in the range of ±10 amino acids, of that predicted from either the first methionine codon from the N-terminus shown in FIG. 1A (SEQ ID NO:1).

Leader and Mature Sequences

The amino acid sequence of the complete CLC protein includes a leader sequence and a mature protein, as shown in SEQ ID NO:2. More in particular, the present invention provides nucleic acid molecules encoding a mature form of the CLC protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature CLC polypeptide having the amino acid sequence encoded by the cDNA clone contained in the host identified as ATCC Deposit No. 209122. By the "mature CLC polypeptide having the amino acid sequence encoded by the cDNA clone in ATCC Deposit No. 209122" is meant the mature form(s) of the CLC protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete CLC polypeptide was analyzed by a computer program PSORT, available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis of the CLC amino acid sequence by this program predicted only a single N-terminal cleavage site within the complete amino acid sequence shown in SEQ ID NO:2 between residues −1 and +1.

As indicated, nucleic acid molecules of the present invention may be in the form of RNA, such as MRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 46–48 of the nucleotide sequence shown in FIG. 1A (SEQ ID NO:1).

Also included are DNA molecules comprising the coding sequence for the predicted mature CLC protein shown at positions 1–198 of SEQ ID NO:2.

In addition, isolated nucleic acid molecules of the invention include DNA molecules which comprise a sequence substantially different from those described above but which, due to the degeneracy of the genetic code, still encode the CLC protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the CLC polypeptide having an amino acid sequence encoded by the cDNA clone contained in the plasmid deposited as ATCC Deposit No. 209122 on Jun. 19, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A and 1B (SEQ ID NO:1) or the nucleotide sequence of the CLC cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the CLC gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–723 of SEQ ID NO:1.

In addition, the invention provides nucleic acid molecules having nucleotide sequences related to a portion of SEQ ID NO:1 which has been determined from the related cDNA HNFFQ39 (SEQ ID NO:7; HNFFQ39RA).

Further, the invention includes a polynucleotide comprising any portion of at least about 30 nucleotides, preferably at least about 50 nucleotides, of SEQ ID NO:1 from residue 400 to 900 and from 1375 to 1710. More preferably, the invention includes a polynucleotide comprising nucleotide residues 1–1000, 1–1250, 1–1500, 250–1000, 250–1250, 250–1500, 500–1000, 500–1250, 500–1500, 750–1000, 750–1250, 750–1500, 250–600, 400–600, 1000–1710, 1250–1710, 1000–1250, and 1000–1500. Preferably, such polynucleotides specifically hybridize to the polynucleotide shown in FIGS. 1A and 1B.

More generally, by a fragment of an isolated nucleic acid molecule having the nucleotide sequence of the deposited cDNA or the nucleotide sequence shown in FIGS. 1A and 1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A and 1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A and 1B (SEQ ID NO:1). Preferred nucleic acid fragments of the present invention include nucleic acid molecules encoding epitope-bearing portions of the CLC polypeptide as identified in FIG. 4 and described in more detail below. Preferred nucleic acid fragments of the present invention also include nucleic acid molecules encoding Garnier-Robson and/or Chou-Fasman alpha, beta, and/or turn regions, Garnier-Robson coil regions, Kyte-Doolittle hydrophilic regions, Hopp-Woods hydrophobic regions, Eisenberg alpha and/or beta amphipathic regions, Karplus-Schulz flexible regions, Jameson-Wolf antigenic regions, and/or Emini surface probability regions of the CLC polypeptide as identified in FIG. 4 or in a tabular representation of the data presented in FIG. 4 (as generated by the "Protean" or "Protein Analysis" module of the Lasergene (DNA*STAR) computer software program).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209122. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A and 1B (SEQ ID NO:1)). Of course, a polynucleotide which hybridizes only to a poly A sequence (such as the 3' terminal poly(A) tract of the CLC cDNA shown in FIG. 1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a CLC polypeptide may include, but are not limited to those encoding the amino acid sequence of the mature polypeptide, by itself; and the coding sequence for the mature polypeptide and additional sequences, such as those encoding the about 27 amino acid leader or secretory sequence, such as a pre-, or pro- or prepro- protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the CLC fused to Fc at the N- or C-terminus.

Variant and Mutant Polynucleotides

The present invention further relates to variants of the nucleic acid molecules of the present invention, which encode portions, analogs or derivatives of the CLC protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the CLC protein or portions thereof. Also especially preferred in this regard are conservative substitutions.

Most highly preferred are nucleic acid molecules encoding the mature protein having the amino acid sequence shown in SEQ ID NO:2 or the mature CLC amino acid sequence encoded by the deposited cDNA clone.

Further embodiments include an isolated nucleic acid molecule comprising a polynucleotide having a nucleotide sequence at least 90% identical to (or at most 10% different from), and more preferably at least 95%, 96%, 97%, 98% or 99% identical to (or at most 5%, 4%, 3%, 2% or 1% different from) a polynucleotide selected from the group consisting of: (a) a nucleotide sequence encoding the CLC polypeptide having the complete amino acid sequence in SEQ ID NO:2 (i.e., positions –27 to 198 of SEQ ID NO:2); (b) a nucleotide sequence encoding the CLC polypeptide having the complete amino acid sequence in SEQ ID NO:2 excepting the N-terminal methionine (i.e., positions –26 to 198 of SEQ ID NO:2); (c) a nucleotide sequence encoding the predicted mature CLC polypeptide having the amino acid sequence at positions 1 to 198 in SEQ ID NO:2; (d) a nucleotide sequence encoding the CLC polypeptide having the complete amino acid sequence encoded by the cDNA clone contained in ATCC Deposit No. 209122; (e) a nucleotide sequence encoding the CLC polypeptide having the complete amino acid sequence excepting the N-terminal methionine encoded by the cDNA clone contained in ATCC Deposit No. 209122; (f) a nucleotide sequence encoding the mature CLC polypeptide having the amino acid sequence encoded by the cDNA clone contained in ATCC Deposit No. 209122; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical to (or at most 10% different from), and more preferably at least 95%, 96%, 97%, 98% or 99% identical to (or at most 5%, 4%, 3%, 2% or 1% different from), any of the nucleotide sequences in (a), (b), (c), (d), (e), (f), or (g) above, or a polynucleotide which hybridizes under stringent hybridization conditions to a polynucleotide in (a), (b), (c), (d), (e) or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a CLC polypeptide having an amino acid sequence in (a), (b), (c), (d), (e), or (g) above.

The present invention also relates to recombinant vectors, which include the isolated nucleic acid molecules of the present invention, and to host cells containing the recombinant vectors, as well as to methods of making such vectors and host cells and for using them for production of CLC polypeptides or peptides by recombinant techniques.

By a polynucleotide having a nucleotide sequence at least, for example, 95% "identical" to a reference nucleotide sequence encoding a CLC polypeptide is intended that the nucleotide sequence of the polynucleotide is identical to the reference sequence except that the polynucleotide sequence may include up to five point mutations per each 100 nucleotides of the reference nucleotide sequence encoding the CLC polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to (or at most 5%, 4%, 3%, 2% or 1% different from), for instance, the nucleotide sequence shown in FIGS. 1A and 1B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequnce are manually corrected for. No other manual corrections are to made for the purposes of the present invention.

The present application is directed to nucleic acid molecules at least 90%, 95%, 96%, 97%, 98% or 99% identical to (or at most 10%, 5%, 4%, 3%, 2% or 1% different from) the nucleic acid sequence shown in FIGS. 1A and 1B (SEQ ID NO:1) or to the nucleic acid sequence of the deposited cDNA, irrespective of whether they encode a polypeptide having CLC activity. This is because even where a particular nucleic acid molecule does not encode a polypeptide having CLC activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CLC activity include, inter alia, (1) isolating the CLC gene or allelic variants thereof in a cDNA library; (2) in situ hybridization (e.g., "FISH") to metaphase chromosomal spreads to provide precise chromosomal location of the CLC gene, as described in Verma et al., Human Chromosomes: A Manual of Basic Techniques, Pergamon Press, New York (1988); and Northern Blot analysis for detecting CLC mRNA expression in specific tissues.

Preferred, however, are nucleic acid molecules having sequences at least 90%, 95%, 96%, 97%, 98% or 99% identical to (or at most 10%, 5%, 4%, 3%, 2% or 1% different from) the nucleic acid sequence shown in FIGS. 1A and 1B (SEQ ID NO:1) or to the nucleic acid sequence of the deposited cDNA which do, in fact, encode a polypeptide having CLC protein activity. By "a polypeptide having CLC activity" is intended polypeptides exhibiting activity similar, but not necessarily identical, to an activity of the mature CLC protein of the invention, as measured in a particular biological assay. For example, the CLC protein of the present invention modulates the growth and differentiation of cardiac and hematopoietic cells as does CT-1. The initial step in such an activity is a physical interaction with, and subsequent binding to, one or more receptor molecules. An in vitro CT-1 receptor-binding assay has been described by Pennica and colleagues (J. Biol. Chem. 270:10915–10922; 1995) and Layton and coworkers (J. Biol. Chem. 269:17048–17055; 1994). Briefly, the assay involves allowing recombinantly tagged gp 130 and LIF receptor proteins (that is, the components of the CT-1 receptor) to interact with candidate CT-1 or CLC proteins or muteins in vitro and determining the relative amount of receptor binding which occurs by quantitation of radioactively tagged receptor protein. More specifically, receptor-binding assays are performed in 96-well Multiscreen-HV filtration plates with 0.45 mM polyvinylidene difluoride membranes (Millipore) in phosphate-buffered saline (PBS) containing 0.1% bovine serum albumin and including 25 ml of PBS-washed $Ni^{2+}$-agarose (Qiagen) in a final volume of 175 ml. Plates are incubated at room temperature overnight with agitation. Following vacuum filtration and one wash with 200 ml of cold PBS, the individual assay wells are cut from the plate and counted. Such activity is useful for determining receptor binding.

CLC protein modulates immune system cell proliferation and differentiation in a dose-dependent manner in the above-described assay. Thus, "a polypeptide having CLC protein activity" includes polypeptides that also exhibit any of the same receptor-binding and growth regulation activities in the above-described assays in a dose-dependent manner. Although the degree of dose-dependent activity need not be identical to that of the CLC protein, preferably, "a polypeptide having CLC protein activity" will exhibit substantially similar dose-dependence in a given activity as compared to the CLC protein (i.e., the candidate polypeptide will exhibit greater activity or not more than about 25-fold less and, preferably, not more than about tenfold less activity relative to the reference CLC protein).

Of the known members of the IL-6 cytokine family, CLC exhibits the highest degree of sequence relatedness to CT-1. A primary function of CT-1 is regulation of the hypertrophic response of cardiomyocytes. Based on sequence identity, CLC also functions in the regulation of various hypertrophic responses of cardiomyocytes. An invariant characteristic of cardiomyocyte hypertrophy in response to stimulation by CT-1 is the stimulation of MAP kinase-dependent signal transduction pathways. The response of neonatal rat ventricular cardiomyocyte cells to CT-1, CLC, and/or muteins thereof, may be easily assayed by using a MAP kinase analysis to examine the stimulation of the MAP kinase signal transduction cascade essentially as was described by Wollert and colleagues (J. Biol. Chem. 271:9535–9545; 1996). After plating, cardiac myocytes ($1\times10^6$ cells/6 cm culture dish area) are washed and maintained in serum-free medium for 24 h prior to experimentation. Cells are treated with 1 nM CT-1, LIF, and IL-6 for 12 min, washed with cold PBS, and lysed in Tris-buffered saline containing 1% Triton X-100, 1 mM phenylmethylsulfonyl fluoride, 10 $\mu$g/ml leupeptin, $\mu$g/ml aprotinin, 500 $\mu$M $Na_3VO_4$, and 1 mM NaP2. The cell lysates are carefully collected and protein concentrations are determination (Bio-Rad). Equal amounts of lysate are incubated with anti-ERK1 or anti-ERK2 antibodies (Transduction Laboratories) and protein A-Sepharose CL-4B (Pharmacia Biotech Inc.) for 1 h at 4° C. The precipitate samples are then diluted with a kinase buffer containing 20 mM Hepes, pH 7.0, 2 $\mu$M dithiothreitol, 20 mM ATP, 10 mM MgCl2, 4 $\mu$Ci of [$^{32}$P]-ATP, and 30 $\mu$g of myelin basic protein. After incubation at room temperature for 30 min and boiling for 5 min, equal samples were loaded onto 15% SDS-polyacrylamide gel electrophoresis. The gels are dried and exposed to Kodak X-ray film at –70° C. for 3 h. Relative changes in MAP kinase activity are apparent in the amount of MBP which becomes phosphorylated in response to treatment with CT-1, CLC, and/or muteins thereof.

Of course, due to the degeneracy of the genetic code, one of ordinary skill in the art will immediately recognize that a large number of the nucleic acid molecules having a sequence at least 90%, 95%, 96%, 97%, 98%, or 99% identical to (or at most 10%, 5%, 4%, 3%, 2% or 1% different from) the nucleic acid sequence of the deposited cDNA or the nucleic acid sequence shown in FIGS. 1A and 1B (SEQ ID NO:1) will encode a polypeptide "having CLC protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CLC protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of CLC polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as *E. coli,* Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pHE series, pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from inmmunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The CLC protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated CLC polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of CLC polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.,* 268:2984–2988; 1993) reported modified KGF proteins that had heparin binding activity even if 3, 8, or 27 N-terminal amino acid residues were removed. In the present case, polypeptides having deletions of up to about 10 N -terminal residues (i.e., up to the glycine at position 10 in SEQ ID NO:2 may retain some biological activity such as receptor binding. Polypeptides having further N-terminal deletions including the proline residue at position 11 in SEQ ID NO:2 would not be expected to retain such biological activities.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the CLC shown in SEQ ID NO:2, up to the glycine residue at position number 10, and polynucleotides encoding such polypeptides. In particular, the present invention provides polypeptides comprising the amino acid sequence of residues n–198 of SEQ ID NO:2, where n is an integer in the range of –27 to 10 and 11 is the position of the first residue from the N-terminus of the complete CLC polypeptide (shown in SEQ ID NO:2) believed to be required for receptor binding activity of the CLC protein.

More in particular, the invention provides polynucleotides encoding polypeptides having the amino acid sequence of residues of –27 to 198, –26 to 198, –25 to 198, –24 to 198, –23 to 198, –22 to 198, –21 to 198, –20 to 198, –19 to 198, –18 to 198, –17 to 198, –16 to 198, –15 to 198, –14 to 198, –13 to 198, –12 to 198, –11 to 198, to 198, –9 to 198, –8 to 198, –7 to 198, –6 to 198, –5 to 198, –4 to 198, –3 to 198, –2 to 198, –1 to 198, 1 to 198, 2 to 198, 3 to 198, 4 to 198, 5 to 198, 6 to 198, 7 to 198, 8 to 198, 9 to 198, 10 to 198, and 11 to 198 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dobeli et al., *J. Biotechnology* 7:199–216; 1988). In the present case, polypeptides having deletions of up to about 10 C-terminal residues (i.e., up to the valine at position 189 may retain some biological activity such as receptor binding. Polypeptides having further C-terminal deletions including the valine residue at position 189 of SEQ ID NO:2 would not be expected to retain such biological activities.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the CLC shown in SEQ ID NO:2, up to the valine residue at position 189 of SEQ ID NO:2, and polynucleotides encoding such polypeptides. In particular, the present invention provides polypeptides having the amino acid sequence of residues –27-m of the amino acid sequence in SEQ ID NO:2, where m is any integer in the range of 188 to 197, and residue 188 is the position of the first residue from the C-terminus of the complete CLC polypeptide (shown in SEQ ID NO:2) believed to be required for receptor binding and growth regulation activities of the CLC protein.

More in particular, the invention provides polynucleotides encoding polypeptides having the amino acid sequence of residues –27 to 188, –27 to 189, –27 to 190, –27 to 191, –27 to 192, –27 to 193, –27 to 194, –27 to 195, –27 to 196, –27 to 197, and –27 to 198 of SEQ ID NO:2. Polynucleotides encoding these polypeptides also are provided.

The invention also provides polypeptides having one or more amino acids deleted from both the amino and the carboxyl termini, which may be described generally as having residues n–m of SEQ ID NO:2, where n and m are integers as described above.

Also included are a nucleotide sequence encoding a polypeptide consisting of a portion of the complete CLC amino acid sequence encoded by the cDNA clone contained in ATCC Deposit No. 209122, where this portion excludes from 1 to about 36 amino acids from the amino terminus of the full-length amino acid sequence encoded by the cDNA clone contained in ATCC Deposit No. 209122, or from 1 to about 10 amino acids from the carboxy terminus, or any combination of the above amino terminal and carboxy terminal deletions, of the complete amino acid sequence encoded by the cDNA clone contained in ATCC Deposit No. 209122. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened CLC mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that an CLC mutein with a large number of deleted N-terminal amino acid residues may retain some biological or immungenic activities. In fact, peptides composed of as few as six CLC amino acid residues may often evoke an immune response.

Accordingly, the present invention further provides polypeptides having one or more residues deleted from the amino terminus of the predicted mature amino acid sequence of the CLC shown in SEQ ID NO:2, up to the leucine residue at position number 193 and polynucleotides encoding such polypeptides. In particular, the present invention provides polypeptides comprising the amino acid sequence of residues n'-198 of SEQ ID NO:2, where n' is an integer in the range of –27 to 193, and 193 is the position of the first residue from the N-terminus of the complete CLC polypeptide believed to be required for at least immunogenic activity of the CLC protein.

More in particular, the invention provides polynucleotides encoding polypeptides comprising, or alternatively consisting of, the amino acid sequence of residues of M-(–27) to F-198; D-(–26) to F-198; L-(–25) to F-198; R-(–24) to F-198; A-(–23) to F-198; G-(–22) to F-198; D-(–21) to F-198; S-(–20) to F-198; W-(–19) to F-198; G-(–18) to F-198; M-(–17) to F-198; L-(–16) to F-198; A-(–15) to F-198; C-(–14) to F-198; L-(–13) to F-198; C-(–12) to F-198; T-(–11) to F-198; V-(–10) to F-198; L-(–9) to F-198; W-(–8) to F-198; H-(–7) to F-198; L-(–6) to F-198; P-(–5) to F-198; A-(–4) to F-198; V-(–3) to F-198; P-(–2) to F-198; A-(–1) to F-198; L-1 to F-198; N-2 to F-198; R-3 to F-198; T-4 to F-198; G-5 to F-198; D-6 to F-198; P-7 to F-198; G-8 to F-198; P-9 to F-198; G-10 to F-198; P-11 to F-198; S-12 to F-198; I-13 to F-198; Q-14 to F-198; K-15 to F-198; T-16 to F-198; Y-17 to F-198; D-18 to F-198; L-19 to F-198; T-20 to F-198; R-21 to F-198; Y-22 to F-198; L-23 to F-198; E-24 to F-198; H-25 to F-198; Q-26 to F-198; L-27 to F-198; R-28 to F-198; S-29 to F-198; L-30 to F-198; A-31 to F-198; G-32 to F-198; T-33 to F-198; Y-34 to F-198; L-35 to F-198; N-36 to F-198; Y-37 to F-198; L-38 to F-198; G-39 to F-198; P-40 to F-198; P-41 to F-198; F-42 to F-198; N-43 to F-198; E-44 to F-198; P-45 to F-198; D-46 to F-198; F-47 to F-198; N-48 to F-198; P-49 to F-198; P-50 to F-198; R-51 to F-198; L-52 to F-198; G-53 to F-198; A-54 to F-198; E-55 to F-198; T-56 to F-198; L-57 to F-198; P-58 to F-198; R-59 to F-198; A-60 to F-198; T-61 to F-198; V-62 to F-198; D-63 to F-198; L-64 to F-198; E-65 to F-198; V-66 to F-198; W-67 to F-198; R-68 to F-198; S-69 to F-198; L-70 to F-198; N-71 to F-198; D-72 to F-198; K-73 to F-198; L-74 to F-198; R-75 to F-198; L-76 to F-198; T-77 to F-198; Q-78 to F-198; N-79 to F-198; Y-80 to F-198; E-81 to F-198; A-82 to F-198; Y-83 to F-198; S-84 to F-198; H-85 to F-198; L-86 to F-198; L-87 to F-198; C-88 to F-198; Y-89 to F-198; L-90 to F-198; R-91 to F-198; G-92 to F-198; L-93 to F-198; N-94 to F-198; R-95 to F-198; Q-96 to F-198; A-97 to F-198; A-98 to F-198; T-99 to F-198; A-100 to F-198; E-101 to F-198; L-102 to F-198; R-103 to F-198; R-104 to F-198; S-105 to F-198; L-106 to F-198; A-107 to F-198; H-108 to F-198; F-109 to F-198; C-110 to F-198; T-111 to F-198; S-112 to F-198; L-113 to F-198; Q-114 to F-198; G-115 to F-198; L-116 to F-198; L-117 to F-198; G-118 to F-198; S-119 to F-198; I-120 to F-198; A-121 to F-198; G-122 to F-198; V-123 to F-198; M-124 to F-198; A-125 to F-198; A-126 to F-198; L-127 to F-198; G-128 to F-198; Y-129 to F-198; P-130 to F-198; L-131 to F-198; P-132 to F-198; Q-133 to F-198; P-134 to F-198; L-135 to F-198; P-136 to F-198; G-137 to F-198; T-138 to F-198; E-139 to F-198; P-140 to F-198; T-141 to F-198; W-142 to F-198; T-143 to F-198; P-144 to F-198; G-145 to F-198; P-146 to F-198; A-147 to F-198; H-148 to F-198; S-149 to F-198; D-150 to F-198; F-151 to F-198; L-152 to F-198; Q-153 to F-198; K-154 to F-198; M-155 to F-198; D-156 to F-198; D-157 to F-198; F-158 to F-198; W-159 to F-198; L-160 to F-198; L-161 to F-198; K-162 to F-198; E-163 to F-198; L-164 to F-198; Q-165 to F-198; T-166 to F-198; W-167 to F-198; L-168 to F-198; W-169 to F-198; R-170 to F-198; S-171 to F-198; A-172 to F-198; K-173 to F-198; D-174 to F-198; F-175 to F-198; N-176 to F-198; R-177 to F-198; L-178 to F-198; K-179 to F-198; K-180 to F-198; K-181 to F-198; M-182 to F-198; Q-183 to F-198; P-184 to F-198; P-185 to F-198; A-186 to F-198; A-187 to F-198; A-188 to F-198; V-189 to F-198; T-190 to F-198; L-191 to F-198; H-192 to F-198; and L-193 to F-198 of the CLC sequence shown in SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other biological activities may still be retained. Thus, the ability of the shortened CLC mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a CLC mutein with a large number of deleted C-terminal amino acid residues may retain some biological or immungenic activities. In fact, peptides composed of as few as six CLC amino acid residues may often evoke an immune response.

Accordingly, the present invention further provides polypeptides having one or more residues deleted from the carboxy terminus of the amino acid sequence of the CLC shown in SEQ ID NO:2, up to the aspartic acid residue at position number −21, and polynucleotides encoding such polypeptides. In particular, the present invention provides polypeptides comprising the amino acid sequence of residues 1–m' of SEQ ID NO:2, where m' is an integer in the range of −21 to 198, and −22 is the position of the first residue from the C-terminus of the complete CLC polypeptide believed to be required for at least immunogenic activity of the CLC protein.

More in particular, the invention provides polynucleotides encoding polypeptides comprising, or alternatively consisting of, the amino acid sequence of residues M-(−27) to G-197; M-(−27) to H-196; M-(−27) to A-195; M-(−27) to G-194; M-(−27) to L-193; M-(−27) to H-192; M-(−27) to L-191; M-(−27) to T-190; M-(−27) to V-189; M-(−27) to A-188; M-(−27) to A-187; M-(−27) to A-186; M-(−27) to P-185; M-(−27) to P-184; M-(−27) to Q-183; M-(−27) to M-182; M-(−27) to K-181; M-(−27) to K-180; M-(−27) to K-179; M-(−27) to L-178; M-(−27) to R-177; M-(−27) to N-176; M-(−27) to F-175; M-(−27) to D-174; M-(−27) to K-173; M-(−27) to A-172; M-(−27) to S-171; M-(−27) to R-170; M-(−27) to W-169; M-(−27) to L-168; M-(−27) to W-167; M-(−27) to T-166; M-(−27) to Q-165; M-(−27) to L-164; M-(−27) to E-163; M-(−27) to K-162; M-(−27) to L-161; M-(−27) to L-160; M-(−27) to W-159; M-(−27) to F-158; M-(−27) to D-157; M-(−27) to D-156; M-(−27) to M-155; M-(−27) to K-154; M-(−27) to Q-153; M-(−27) to L-152; M-(−27) to F-151; M-(−27) to D-150; M-(−27) to S-149; M-(−27) to H-148; M-(−27) to A-147; M-(−27) to P-146; M-(−27) to G-145; M-(−27) to P-144; M-(−27) to T-143; M-(−27) to W-142; M-(−27) to T-141; M-(−27) to P-140; M-(−27) to E-139; M-(−27) to T-138; M-(−27) to G-137; M-(−27) to P-136; M-(−27) to L-135; M-(−27) to P-134; M-(−27) to Q-133; M-(−27) to P-132; M-(−27) to L-131; M-(−27) to P-130; M-(−27) to Y-129; M-(−27) to G-128; M-(−27) to L-127; M-(−27) to A-126; M-(−27) to A-125; M-(−27) to M-124; M-(−27) to V-123; M-(−27) to G-122; M-(−27) to A-121; M-(−27) to I-120; M-(−27) to S-119; M-(−27) to G-118; M-(−27) to L-117; M-(−27) to L-116; M-(−27) to G-115; M-(−27) to Q-114; M-(−27) to L-113; M-(−27) to S-112; M-(−27) to T-111; M-(−27) to C-110; M-(−27) to F-109; M-(−27) to H-108; M-(−27) to A-107; M-(−27) to L-106; M-(−27) to S-105; M-(−27) to R-104; M-(−27) to R-103; M-(−27) to L-102; M-(−27) to E-101; M-(−27) to A-100; M-(−27) to T-99; M-(−27) to A-98; M-(−27) to A-97; M-(−27) to Q-96; M-(−27) to R-95; M-(−27) to N-94; M-(−27) to L-93; M-(−27) to G-92; M-(−27) to R-91; M-(−27) to L-90; M-(−27) to Y-89; M-(−27) to C-88; M-(−27) to L-87; M-(−27) to L-86; M-(−27) to H-85; M-(−27) to S-84; M-(−27) to Y-83; M-(−27) to A-82; M-(−27) to E-81; M-(−27) to Y-80; M-(−27) to N-79; M-(−27) to Q-78; M-(−27) to T-77; M-(−27) to L-76; M-(−27) to R-75; M-(−27) to L-74; M-(−27) to K-73; M-(−27) to D-72; M-(−27) to N-71; M-(−27) to L-70; M-(−27) to S-69; M-(−27) to R-68; M-(−27) to W-67; M-(−27) to V-66; M-(−27) to E-65; M-(−27) to L-64; M-(−27) to D-63; M-(−27) to V-62; M-(−27) to T-61; M-(−27) to A-60; M-(−27) to R-59; M-(−27) to P-58; M-(−27) to L-57; M-(−27) to T-56; M-(−27) to E-55; M-(−27) to A-54; M-(−27) to 6–53; M-(−27) to L-52; M-(−27) to R-51; M-(−27) to P-50; M-(−27) to P-49; M-(−27) to N-48; M-(−27) to F-47; M-(−27) to D-46;

M-(−27) to P-45; M-(−27) to E-44; M-(−27) to N-43; M-(−27) to F-42; M-(−27) to P-41; M-(−27) to P-40; M-(−27) to G-39; M-(−27) to L-38; M-(−27) to Y-37; M-(−27) to N-36; M-(−27) to L-35; M-(−27) to Y-34; M-(−27) to T-33; M-(−27) to 6-32; M-(−27) to A-3 1; M-(−27) to L-30; M-(−27) to S-29; M-(−27) to R-28; M-(−27) to L-27; M-(−27) to Q-26; M-(−27) to H-25; M-(−27) to E-24; M-(−27) to L-23; M-(−27) to Y-22; M-(−27) to R-21; M-(−27) to T-20; M-(−27) to L-19; M-(−27) to D-18; M-(−27) to Y-17; M-(−27) to T-16; M-(−27) to K-35; M-(−27) to Q-14; M-(−27) to I-13; M-(−27) to S-12; M-(−27) to P-11; M-(−27) to 6-10; M-(−27) to P-9; M-(−27) to 6-8; M-(−27) to P-7; M-(−27) to D-6; M-(−27) to 6-5; M-(−27) to T-4; M-(−27) to R-3; M-(−27) to N-2; M-(−27) to L-1; M-(−27) to A-(−1); M-(−27) to P-(−2); M-(−27) to V-(−3); M-(−27) to A-(−4); M-(−27) to P-(−5); M-(−27) to L-(−6); M-(−27) to H-(−7); M-(−27) to W-(−8); M-(−27) to L-(−9); M-(−27) to V-(−10); M-(−27) to T-(−2 1); M-(−27) to C-(−12); M-(−27) to L-(−43); M-(−27) to C-(−54); M-(−27) to A-(−15); M-(−27) to L-(−16); M-(−27) to M-(−97); M-(−27) to V-(−18); M-(−27) to W-(−19); M-(−27) to S-(−20); and M-(−27) to D-(−21) of the sequence of the CLC sequence shown in SEQ ID NO:2. Polynucleotides encoding these polypeptides also are provided.

The invention also provides polypeptides having one or more amino acids deleted from both the amino and the carboxyl termini of a CLC polypeptide, which may be described generally as having residues n'–m' of SEQ ID NO:2, where n' and m' are integers as described above.

Other Mutants

In addition to terminal deletion forms of the protein discussed above, it also will be recognized by one of ordinary skill in the art that some amino acid sequences of the CLC polypeptide can be varied without significant effect of the structure or function of the protein. If such differences in sequence are contemplated, it should be remembered that there will be critical areas on the protein which determine activity.

An alignment of the CLC amino acid sequence of SEQ ID NO:2 with human cardiotrophin (SEQ ID NO:4), LIF (SEQ ID NO:5), and CNTF (SEQ ID NO:6), as presented in FIG. 3, implicates the presence of a number of highly conserved amino acid residues between these polypeptide sequences. In fact, at least three regions of the CLC amino acid sequence appear to be highly conserved with regard to human cardiotrophin, LIF, and CNTF. These regions are indicated by a double underline and are labeled conserved domain (CD)-I, CD-II, and CD-III in FIG. 1A. In addition, a large number of individual leucine residues in the CLC polypeptide also appear to be highly conserved within this group of polypeptide sequences. For example, the leucine residues at the following positions of SEQ ID NO:2 appear in analogous positions in at least two of the other three polypeptide sequences shown in the alignment in FIG. 3: L-(−13), L-19, L-27, L-30, L-52, L-70, L-76, L-86, L-90, L-102, L-106, L-116, L-127, L-160, and L-168. In addition to leucine, a variety of other amino acid residues are also highly conserved including: W-(−8), Y-34, G-39, P-41, F-42, R-75, A-82, R-95, F-151, K-154, and D-174. Such conservation may indicate a potential for involvement of these residues in structural and/or biological function. However, the lists of residues shown above are not limiting in any way and are not meant to disclaim the potential importance of any specific residue in the CLC amino acid sequence not listed above.

Thus, the invention further includes variations of the CLC polypeptide which show substantial CLC polypeptide activity or which include regions of CLC protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the CLC of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

| Conservative Amino Acid Substitutions. | |
|---|---|
| Aromatic | Phenylalanine<br>Tryptophan<br>Tyrosine |

TABLE 1-continued

Conservative Amino Acid Substitutions.

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, deletions or additions in the amino acid sequence of FIGS. 1A and 1B and/or any of the polypeptide fragments described herein is 30, 29, 28, 27, 26, 25, 24, 23, 22, 21, 20, 19, 18, 17, 16, 15, 14, 13, 12 ,11, 10, 9, 8, 7, 6, 5, 4, 3, 2, 1 or 30–20, 20–10, 20–15, 15–10, 10–5 or 1–5.

Amino acids in the CLC protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., Diabetes 36: 838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the CLC polypeptide can be substantially purified by the one-step method described in Smith and Johnson, *Gene* 67:31–40 (1988). Polypeptides of the invention also can be purified from natural or recombinant sources using anti-CLC antibodies of the invention in methods which are well known in the art of protein purification.

The invention further provides an isolated CLC polypeptide comprising an amino acid sequence selected from the group consisting of: (a) the amino acid sequence of the full-length CLC polypeptide having the complete amino acid sequence shown in SEQ ID NO:2 (i.e., positions –27 to 198 of SEQ ID NO:2); (b) the amino acid sequence of the full-length CLC polypeptide having the complete amino acid sequence shown in SEQ ID NO:2 excepting the N-terminal methionine (i.e., positions –26 to 198 of SEQ ID NO:2); (c) the amino acid sequence of the mature CLC polypeptide having the complete amino acid sequence shown in SEQ ID NO:2 (i.e., positions 1 to 198 of SEQ ID NO:2); (d) the amino acid sequence of the full-length CLC polypeptide encoded by the cDNA clone contained in ATCC Deposit No. 209122; (e) the amino acid sequence of the full-length CLC polypeptide having the complete amino acid sequence, excepting the N-terminal methionine, encoded by the cDNA clone contained in ATCC Deposit No. 209122, and; (f) the amino acid sequence of the full-length CLC polypeptide having the complete amino acid sequence, excepting the N-terminal methionine, encoded by the cDNA clone contained in ATCC Deposit No. 209122.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference or query amino acid sequence of a CLC polypeptide is intended that the amino acid sequence of the polypeptide is identical to the reference sequence except that the polypeptide sequence may include up to five amino acid alterations per each 100 amino acids of the reference amino acid of the CLC polypeptide. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C- termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting CLC protein expression as described below or as agonists and antagonists capable of enhancing or inhibiting CLC protein function. Further, such polypeptides can be used in the yeast two-hybrid system to "capture" CLC protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (Geysen et al., *Proc. Natl. Acad. Sci. USA* 81:3998–4002; 1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science,* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate CLC-specific antibodies include: a polypeptide comprising amino acid residues from about Leu-1 to about Pro-9, from about Ser-12 to about Thr-20, from about Phe-42 to about Pro-50, from about Leu-52 to about Ala-60, from about Asn-71 to about Glu-92, from about Asn-94 to about Arg-104, from about Leu-135 to about Pro-144, from about His-148 to about Asp-157, and from about Asp-174 to about Gln-183. These polypeptide fragments have been determined to bear antigenic epitopes of the CLC protein by the analysis of the Jameson-Wolf antigenic index, as shown in FIG. 4, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, CLC polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric CLC protein or protein fragment alone (Fountoulakis et al., *J. Biochem.* 270:3958–3964 (1995)).

Antibodies

CLC-protein specific antibodies for use in the present invention can be raised against the intact CLC protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules, single chain whole antibodies, and antibody fragments. Antibody fragments of the present invention include Fab and F(ab')2 and other fragments including single-chain Fvs (scFv) and disulfide-linked Fvs (sdFv). Also included in the present invention are chimeric and humanized monoclonal antibodies and polyclonal antibodies specific for the polypeptides of the present invention. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the CLC protein or an antigenic fragment thereof can be administered to an animal in order to induce the production of sera containing polyclonal antibodies. In a preferred method, a preparation of CLC protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or CLC protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., (1981) pp. 563–681 ). In general, such procedures involve immunizing an animal (preferably a mouse) with a CLC protein antigen or, more preferably, with a CLC protein-expressing cell. Suitable cells can be recognized by their capacity to bind anti-CLC protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the CLC protein antigen.

Alternatively, additional antibodies capable of binding to the CLC protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, CLC-protein specific antibodies are used to immunize an animal, preferably a mouse. The splenocytes of such an animal are then used to produce hybridoma cells, and the hybridoma cells are screened to identify clones which produce an antibody whose ability to bind to the CLC protein-specific antibody can be blocked by the CLC protein antigen. Such antibodies comprise anti-idiotypic antibodies to the CLC protein-specific antibody and can be used to immunize an animal to induce formation of further CLC protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, CLC protein-binding fragments can be produced through the application of recombinant DNA technology or through synthetic chemistry.

For in vivo use of anti-CLC in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Antibodies and fragements thereof of the present invention may be described by the portion of a polypeptide of the present invention recognized or specifically bound by the antibody. Antibody binding fragments of a polypeptide of the present invention may be described or specified in the same manner as for polypeptide fragments discussed above., i.e, by N- and C-terminal positions or by size in contiguous amino acid residues. Any number of antibody binding fragments, of a polypeptide of the present invention, specified by N- and C-terminal positions or by size in amino acid residues, as described above, may also be excluded from the present invention. Therefore, the present invention includes antibodies the specifically bind a particularly discribed fragment of a polypeptide of the present invention and allows for the exclusion of the same.

Cardiac and Immune System-Related Disorders
Diagnosis

The present inventors have discovered that CLC is expressed in activated neutrophils, bone marrow stromal cells, synovial fibroblasts, peripheral blood mononuclear cells, and ovarian tumor cells. For a number of immune system-related disorders, substantially altered (increased or decreased) levels of CLC gene expression can be detected in immune system tissue or other cells or bodily fluids (e.g., sera, plasma, urine, synovial fluid or spinal fluid) taken from an individual having such a disorder, relative to a "standard" CLC gene expression level, that is, the CLC expression level in immune system tissues or bodily fluids from an individual not having the immune system disorder. Thus, the invention provides a diagnostic method useful during diagnosis of an immune system disorder, which involves measuring the expression level of the gene encoding the CLC protein in immune system tissue or other cells or body fluid from an individual and comparing the measured gene expression level with a standard CLC gene expression level, whereby an increase or decrease in the gene expression level compared to the standard is indicative of an immune system disorder.

In particular, it is believed that certain tissues in mammals with cancers of the immune system express significantly reduced levels of the CLC protein and mRNA encoding the CLC protein when compared to a corresponding "standard" level. Further, it is believed that enhanced levels of the CLC protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of an immune system disorder, including cancers of this system, which involves measuring the expression level of the gene encoding the CLC protein in immune system tissue or other cells or body fluid from an individual and comparing the measured gene expression level with a standard CLC gene expression level, whereby an increase or decrease in the gene expression level compared to the standard is indicative of an immune system disorder.

Where a diagnosis of a disorder in the immune system including diagnosis of a tumor, has already been made according to conventional methods, the present invention is useful as a prognostic indicator, whereby patients exhibiting altered CLC gene expression will experience a worse clinical outcome relative to patients expressing the gene at a level nearer the standard level.

By "assaying the expression level of the gene encoding the CLC protein" is intended qualitatively or quantitatively measuring or estimating the level of the CLC protein or the level of the mRNA encoding the CLC protein in a first biological sample either directly (e.g., by determining or estimating absolute protein level or mRNA level) or relatively (e.g., by comparing to the CLC protein level or mRNA level in a second biological sample). Preferably, the CLC protein level or mRNA level in the first biological sample is measured or estimated and compared to a standard CLC protein level or mRNA level, the standard being taken from a second biological sample obtained from an individual not having the disorder or being determined by averaging levels from a population of individuals not having a disorder of the immune system. As will be appreciated in the art, once a standard CLC protein level or mRNA level is known, it can be used repeatedly as a standard for comparison.

By "biological sample" is intended any biological sample obtained from an individual, body fluid, cell line, tissue culture, or other source which contains CLC protein or mRNA. As indicated, biological samples include body fluids (such as sera, plasma, urine, synovial fluid and spinal fluid) which contain free CLC protein, immune system tissue, and other tissue sources found to express complete or mature CLC or a CLC receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include any disregulation of immune cell function including, but not limited to, leukemia, atheroscerosis, autoimmune disease, inflammation, metabolic dysfunction, immune-mediated diseases and the like.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the CLC protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying CLC protein levels in a biological sample can occur using antibody-based techniques. For example, CLC protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting CLC protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying CLC protein levels in a biological sample obtained from an individual, CLC protein can also be detected in vivo by imaging. Antibody labels or markers for in vivo imaging of CLC protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A CLC protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain CLC protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, CLC polynucleotides and polypeptides are useful for diagnosis of conditions involving abnormally high or low expression of CLC activities. Given the cells and tissues where CLC is expressed as well as the activities modulated by CLC, it is readily apparent that a substantially altered (increased or decreased) level of expression of CLC in an individual compared to the standard or "normal" level produces pathological conditions related to the bodily system(s) in which CLC is expressed and/or is active.

It will also be appreciated by one of ordinary skill that, since the CLC protein of the invention is a member of the IL-6 cytokine family, the mature secreted form of the protein may be released in soluble form from the cells which express the CLC by proteolytic cleavage. Therefore, when CLC mature form is added from an exogenous source to cells, tissues or the body of an individual, the protein will exert its physiological activities on its target cells of that individual.

Therefore, it will be appreciated that conditions caused by a decrease in the standard or normal level of CLC activity in an individual, particularly disorders of the immune system, can be treated by administration of CLC polypeptide in the form of the mature protein. Thus, the invention also provides a method of treatment of an individual in need of an increased level of CLC activity comprising administering to such an individual a pharmaceutical composition comprising an amount of an isolated CLC polypeptide of the invention, particularly a mature form of the CLC protein of the invention, effective to increase the CLC activity level in such an individual.

CLC may be employed to regulate hematopoiesis, by regulating the activation and differentiation of various hematopoietic progenitor cells, for example, to release mature leukocytes from the bone marrow following chemotherapy, i.e., in stem cell mobilization. CLC may also be employed to treat sepsis. CLC and muteins thereof may be used in the regulation of cardiac muscle cell hypertrophy. There is a need for polypeptides that function as mediators of cardiac hypertrophy, since disturbances of such regulation may be involved in disorders relating to the heart including arrhythmia, inotropia, heart failure, cardiomyopathy, hypertrophy, ischemia, hypertension, valvular or pericardial abnormalities.

Further, CLC may be useful in anti-tumor therapy since there is evidence that the related cytokine IL-6 is useful in this capacity. The polypeptide may be used to regulate the proliferation and differentiation of hematopoietic cells and therefore may be employed to protect bone marrow stem cells from chemotherapeutic agents during chemotherapy. Since CLC, or antagonists thereof, may be used to inhibit growth and/or differentiation of bone marrow cells, the antiproliferative effect may allow administration of higher doses of chemotherapeutic agents and, therefore, more effective chemotherapeutic treatment.

Hypertrophic cardiomyopathy may eventuate heart failure. CLC has cardiomyocyte hypertrophy inhibitory activity, and thus, it may be used as a therapeutic agent to remedy hypertrophic cardiomyopathy and ultimately to diagnose, treat or prevent heart failure or other cardiac disorders such as cardiac arrest, angina, cardiac tumors, and the like.

The polypeptides of the present invention may be useful in inducing a rapid amplification and proliferation of myeloid cells following a myelosuppressive therapeutic treatment. Myelosuppressive treatments include, but are not limited to, those based on administering a therapeutic amount of macrophage inflammatory protein (MIP)-1a, MIP-2a, platelet factor-4 (PF4), IL-8, macrophage chemotactic and activating factor (MCAF), and macrophage inflammatory protein-related protein (MRP)-2. Such treatments are useful for inducing myeloid cells to assume a slow-cycling state thereby providing protection against cell damage caused by, for example, radiation therapy or chemotherapy using cell-cycle active drugs, such as cytosine arabinoside, hydroxyurea, 5-Fu, and Ara-C. Once the chemotherapeutic drug has cleared the system is desirable to stimulate a rapid amplification and proliferation of myeloid cells through the use of an agent such as CLC, either alone or in combination with other myelostimulators, such as GMCSF, GCSF, EPO, and thrombopoietin.

CLC activity is useful for immune enhancement, myeloprotection, stem cell mobilization, acute and chronic inflammatory control and treatment of leukemia. In addition, since CLC has effects on T-cells as well as macrophages, CLC enhances the capacity of antigen presenting cells (APCs) to take up virus, bacteria, or other foreign substances, process them, and present them to the lymphocytes responsible for immune response. In addition, CLC also modulates the interaction of APCs with T-lymphocytes and B-lymphocytes. For instance, CLC provides a costimulation signal during antigen presentation which directs the responding cell to survive, proliferate, differentiate, secrete additional cytokines or soluble mediators. Since APCs have been shown to facilitate the transfer of HIV to CD4+T-cells, CLC also influences this ability and prevents infection of lymphocytes by HIV or other viruses mediated through APCs. This is also true for the initial infection of APCs, T-cells, or other types of cells by HIV, EBV, or any other viruses.

In addition, since CLC directly effects T-cells in vivo, CLC acts as an immune enhancement factor by stimulating the intrinsic activity of T-cells to fight bacterial and viral infection as well as other foregn bodies. Such activities are useful for the normal response to foreign antigens such as infection of allergies as well as immunoresponses to neoplastic or benign growth including both solid tumors and leukemias.

For these reasons, the polypeptide of the present invention is useful for diagnosis or treatment of various immune system-related disorders in mammals, preferably humans. Such disorders include tumors, cancers, and any disregulation of immune cell function including, but not limited to, autoimmunity, arthritis, asthma, leukemias, lymphomas, immunosuppression, sepsis, wound healing, acute and chronic infection, cell medited immunity, humoral immunity, inflammatory bowel disease, myeloprotection, and the like.

Also, as a novel member of the IL-6-related family of cytokine-like factors, CLC may also be useful in the following activities: sympathetic neuron phenotype switching; stimulating survival or proliferation of megakaryocytes, embryonic sensory neurons, and myoblasts; subcutaneous and abdominal fat loss; elevating serum levels of $Ca^{2+}$; increasing hematocrit, platelet, and megakaryocyte counts; B-cell maturation and immunoglobulin secretion; neuronal differentiation; osteoclast activation; acute phase protein response in the liver and in hepatic cells in vitro and in vivo; inhibition of adipocyte differentiation; protection and regeneration of the intestinal epithelial system; growth modulation of solid tumor cells and endothelial cells (including Kaposi's Sarcoma cells); cell survival of ciliary, sympathetic, sensory, motor, preganglionic sympathetic, hippocampal, medial septal neurons and oligodendrocytes; and the like.

Formulations

The CLC polypeptide composition will be formulated and dosed in a fashion consistent with good medical practice, taking into account the clinical condition of the individual patient (especially the side effects of treatment with CLC polypeptide alone), the site of delivery of the CLC polypeptide composition, the method of administration, the scheduling of administration, and other factors known to practitioners. The "effective amount" of CLC polypeptide for purposes herein is thus determined by such considerations.

As a general proposition, the total pharmaceutically effective amount of CLC polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the CLC polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the CLC of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The CLC polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D- (–)-3-hydroxybutyric acid (EP 133,988). Sustained-release CLC polypeptide compositions also include liposomally entrapped CLC polypeptide. Liposomes containing CLC polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal CLC polypeptide therapy.

For parenteral administration, in one embodiment, the CLC polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the CLC polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The CLC polypeptide is typically formulated in such vehicles at a concentration of about 0.1 mg/ml to 100 mg/ml, preferably 1–1 0 mg/ml, at a pH of about 3 to 8. It will be understood that the use of certain of the foregoing excipients, carriers, or stabilizers will result in the formation of CLC polypeptide salts.

CLC polypeptide to be used for therapeutic administration must be sterile. Sterility is readily accomplished by filtration through sterile filtration membranes (e.g., 0.2 micron membranes). Therapeutic CLC polypeptide compositions generally are placed into a container having a sterile access port, for example, an intravenous solution bag or vial having a stopper pierceable by a hypodermic injection needle.

CLC polypeptide ordinarily will be stored in unit or multi-dose containers, for example sealed ampoules or vials, as an aqueous solution or as a lyophilized formulation for reconstitution. As an example of a lyophilized formulation, 10-ml vials are filled with 5 ml of sterile-filtered 1% (w/v) aqueous CLC polypeptide solution, and the resulting mixture is lyophilized. The infusion solution is prepared by reconstituting the lyophilized CLC polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those As which enhance or block the action of CLC on cells, such as its interaction with CLC-binding molecules such as receptor molecules. An agonist is a compound which increases the natural biological functions of CLC or which functions in a manner similar to CLC, while antagonists decrease or eliminate such functions.

In another aspect of this embodiment the invention provides a method for identifying a receptor protein or other ligand-binding protein which binds specifically to a CLC polypeptide. For example, a cellular compartment, such as a membrane or a preparation thereof, may be prepared from a cell that expresses a molecule that binds CLC. The preparation is incubated with labeled CLC and complexes of CLC bound to the receptor or other binding protein are isolated and characterized according to routine methods known in the art. Alternatively, the CLC polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds CLC, such as a molecule of a signaling or regulatory pathway modulated by CLC. The preparation is incubated with labeled CLC in the absence or the presence of a candidate molecule which may be a CLC agonist or antagonist. The ability of the candidate molecule to bind the binding molecule is reflected in decreased binding of the labeled ligand. Molecules which bind gratuitously, i.e., without inducing the effects of CLC on binding the CLC binding molecule, are most likely to be good antagonists. Molecules that bind well and elicit effects that are the same as or closely related to CLC are agonists.

CLC-like effects of potential agonists and antagonists may by measured, for instance, by determining activity of a second messenger system following interaction of the candidate molecule with a cell or appropriate cell preparation, and comparing the effect with that of CLC or molecules that elicit the same effects as CLC. Second messenger systems that may be useful in this regard include but are not limited to AMP guanylate cyclase, ion channel or phosphoinositide hydrolysis second messenger systems.

Another example of an assay for CLC antagonists is a competitive assay that combines CLC and a potential antagonist with membrane-bound CLC receptor molecules or recombinant CLC receptor molecules under appropriate conditions for a competitive inhibition assay. CLC can be labeled, such as by radioactivity, such that the number of CLC molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing CLC-induced activities, thereby preventing the action of CLC by excluding CLC from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of CLC. The antisense RNA oligonucleotide hybridizes to the mRNA in vivo and blocks translation of the mRNA molecule into CLC polypeptide. The oligonucleotides described above can also be delivered to cells such that the antisense RNA or DNA may be expressed in vivo to inhibit production of CLC protein.

The agonists and antagonists may be employed in a composition with a pharmaceutically acceptable carrier, e.g., as described above.

Antagonists, including antibodies directed against various parts of CLC, may be employed for instance to inhibit the chemotaxis and activation of various leukocytes in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the recruitment and activation of mononuclear phagocytes. They may also be employed to treat idiopathic hypereosinophilic syndrome by preventing eosinophil production and migration. Endotoxic shock may also be treated by the antagonists by preventing the migration of macrophages and their production of the human chemokine polypeptides of the present invention. The antagonists may also be employed for treating atherosclerosis, by preventing monocyte infiltration in the artery wall. The antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines. The antagonists may also be employed to treat cases of bone marrow failure, for example, aplastic anemia and myelodysplastic syndrome. The antagonists may also be employed to treat asthma and allergy by preventing eosinophil accumulation in the lung. The antagonists may also be employed to treat subepithelial basement membrane fibrosis which is a prominent feature of the asthmatic lung. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a CLC protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of "His-tagged" CLC in *E. coli*

The bacterial expression vector pQE9 (pD10) is used for bacterial expression in this example. (QIAGEN, Inc., 9259 Eton Avenue, Chatsworth, Calif., 9131 1). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6xHis tag") covalently linked to the amino terminus of that polypeptide.

The DNA sequence encoding the desired portion of the CLC protein comprising the mature form of the CLC amino acid sequence is amplified from the deposited cDNA clone using PCR oligonucleotide primers which anneal to the amino terminal sequences of the desired portion of the CLC protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature form of the CLC protein, the 5' primer has the sequence 5' CGC CCA TGG CTC AAT CGC ACA GGG 3' (SEQ ID NO:8) containing the underlined Nco I restriction site followed by 15 nucleotides of the amino terminal coding sequence of the mature CLC sequence in SEQ ID NO:2. One of ordinary skill in the art would appreciate, of course, that the point in the protein coding sequence where the 5' primer begins may be varied to amplify a DNA segment encoding any desired portion of the complete CLC protein shorter or longer than the mature form of the protein. The 3' primer has the sequence 5° CGC AAG CTT TCA GAA GCC ATG AGC CC 3' (SEQ ID NO:9) containing the underlined Hind III restriction site followed by 17 nucleotides complementary to the 3' end of the coding sequence of the CLC DNA sequence in FIG. 1A.

The amplified CLC DNA fragment and the vector pQE9 are digested with Nco I and Hind III and the digested DNAs are then ligated together. Insertion of the CLC DNA into the restricted pQE9 vector places the CLC protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual, 2nd Ed.;* Cold Spring Harbor Laboratory Press, Cold Spring Harbor, N.Y. (1989). *E. coli* strain M 15/rep4, containing multiple copies of the plasmid pREP4, which expresses the lac repressor and confers kanamycin resistance ("Kanr"), is used in carrying out the illustrative example described herein. This strain, which is only one of many that are suitable for expressing CLC protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture is used to inoculate a large culture, at a dilution of approximately 1:25 to 1:250. The cells are grown to an optical density at 600 nm ("OD600") of between 0.4 and 0.6. Isopropyl-$\beta$-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the CLC is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the CLC is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify CLC expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000 ×g centrifugation for 15 min., the pellet is discarded and the CLC polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded CLC polypeptide solution, a previously prepared tangential filtration unit equipped with 0.16 $\mu$m membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the CLC polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the CLC polypeptide (determined, for instance, by 16% SDS-PAGE) are then pooled.

The resultant CLC polypeptide exhibits greater than 95% purity after the above refolding and purification steps. No major contaminant bands are observed from Commassie blue stained 16% SDS-PAGE gel when 5 $\mu$g of purified protein is loaded.

The purified protein is also tested for endotoxin/LPS contamination, and typically the LPS content is less than 0.1 ng/ml according to LAL assays.

Example 2

Cloning and Expression of CLC protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature CLC protein, using standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

The cDNA sequence encoding the full length CLC protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5° CGC GGA TCC ATG GAC CTC CGA GCA GGG 3' (SEQ ID NO:10) containing the underlined Bam HI restriction enzyme site, an efficient signal for initiation of translation in eukaryotic cells, as described by Kozak, M., *J. Mol. Biol.* 196:947–950 (1987), followed by 15 nucleotides of the sequence of the complete CLC protein shown in FIG. 1A, beginning with the AUG initiation codon. The 3' primer has the sequence 5° CGC GGT ACC TCA GAA GCC ATG AGC CC 3' (SEQ ID NO:11) containing the underlined Asp 718 restriction site followed by 17 nucleotides complementary to the 3' noncoding sequence in FIG. 1A.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human CLC gene by digesting DNA from individual colonies using Bam HI and Asp 718 and then analyzing the digestion product by gel electrophoresis. The sequence of the cloned fragment is confirmed by DNA sequencing. This plasmid is designated herein pA2-CLC.

Five μg of the plasmid pA2-CLC is co-transfected with 1.0 μg of a commercially available linearized baculovirus DNA ("BaculoGold™ baculovirus DNA", Pharmingen, San Diego, Calif.), using the lipofection method described by Felgner ct al., *Proc. Natl. Acad. Sci. USA* 84: 7413–7417 (1987). One μg of BaculoGold™ virus DNA and 5 μg of the plasmid pA2-CLC are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-CLC.

To verify the expression of the CLC gene Sf9 cells are grown in Grace's medium supplemented with 10% heat-inactivated FBS. The cells are infected with the recombinant baculovirus V-CLC at a multiplicity of infection ("MOI") of about 2. If radiolabeled proteins are desired, 6 hours later the medium is removed and is replaced with SF900 II medium minus methionine and cysteine (available from Life Technologies Inc., Rockville, MD). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the CLC protein and thus the cleavage point and length of the naturally associated secretory signal peptide.

Example 3

Cloning and Expression of CLC in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the gene can be expressed in-stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pCLCHA, is made by cloning a portion of the cDNA encoding the mature form of the CLC protein into the expression vector pcDNAI/Amp or pcD-NAIII (which can be obtained from Invitrogen, Inc.).

The expression vector pcDNAI/amp contains: (I) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the mature CLC polypeptide is cloned into the polylinker region of the vector so that recombinant protein expression is directed by the CMV promoter. The plasmid construction strategy is as follows. The CLC cDNA of the deposited clone is amplified using primers that contain convenient restriction sites, much as described above for construction of vectors for expression of CLC in *E. coli.* Suitable primers include the following, which are used in this example. The 5' primer, containing the underlined Bam HI site, a Kozak sequence, an AUG start codon, and 15 nucleotides of the 5' coding region of the mature CLC polypeptide, has the following sequence: 5' GCC GGA TCC GCC ACC ATG AAC TCC TTC TCC ACA AGC GCC TTC GGT CCA GTT GCC TTC TCC CTG GGG CTG CTC CTG GTG TTG CCT GCT GCC TTC CCT GCC CCA GTA TGG ACC TCC GAG CAG GG 3' (SEQ ID NO:12). The 3' primer, containing the underlined Asp 718 and 17 of nucleotides complementary to the 3' coding sequence immediately before the stop codon, has the following sequence: 5' GGC CGG GTA CCT CAG AAG CCA TGA GCC C 3' (SEQ ID NO:13).

The PCR amplified DNA fragment and the vector, pcDNAI/Amp, are digested with Bam HI and Asp 718 and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the mature CLC polypeptide.

For expression of recombinant CLC, COS cells are transfected with an expression vector, as described above, using DEAE-DEXTRAN, as described, for instance, in Sambrook et al., *Molecular Cloning: a Laboratory Manual,* Cold Spring Laboratory Press, Cold Spring Harbor, N.Y. (1989). Cells are incubated under conditions for expression of CLC by the vector.

Expression of the CLC-HA fusion protein is detected by radiolabeling and immunoprecipitation, using methods described in, for example Harlow et al., *Antibodies: A Laboratory Manual, 2nd Ed.;* Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of CLC polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology,* March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the CLC polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the mature CLC polypeptide is amplified using PCR oligonucleotide primers corresponding to the 5' and 3' sequences of the desired portion of the gene. The 5' primer containing the underlined Bam HI site, a Kozak sequence (in italics), an AUG start codon, and 15 nucleotides of the 5' coding region of the mature CLC polypeptide, has the following sequence: 5° CTA GCC GGA TCC GCC ACC ATG GAC CTC CGA GCA GGG 3' (SEQ ID NO:14). The 3' primer, containing the underlined Asp 718 and 17 of nucleotides complementary to the 3' coding sequence immediately before the stop codon as shown in FIG. 1A (SEQ ID NO:1), has the following sequence: 5' GGC CGG GTA CCT CAG AAG CCA TGA GCC C 3' (SEQ ID NO:13).

The amplified fragment is digested with the endonucleases Bam HI and Asp 718 and then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of CLC mRNA Expression

Northern blot analysis is carried out to examine CLC gene expression in human tissues, using methods described by, among others, Sambrook et al., cited above. A cDNA probe containing the entire nucleotide sequence of the CLC protein (SEQ ID NO:1) is labeled with $^{32}p$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT 1200-1. The purified labeled probe is then used to examine various human tissues for CLC mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT 1190-1. Following hybridization and washing, the blots are mounted and exposed to film at −70° C. overnight, and films developed according to standard procedures.

Northern blot experiments have been performed essentially as described above.

Northern blot analysis indicates that CLC is expressed in spleen, testis, and leukocytes.

The tissues that show a CLC signal by Northern blot are mostly related to immune functions or hematopoiesis.

Example 5

Initial Experimental Analysis of CLC Signaling Mechanisms

The Protein Tyrosine Kinases (PTK) represent a diverse group of transmembrane and cytoplasmic kinases. Within the receptor protein tyrosine kinase (RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, Ick, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether CLC or a molecule induced by CLC is capable of activating tyrosine kinase signal transduction pathways is of interest. Therefore, the following protocol is designed to identify such molecules capable of activating the tyrosine kinase signal transduction pathways.

Seed NIH-3T3 cells in 15 cm$^2$ cell culture plates in DMEM supplemented with Pen/Strep, 10% FBS, 25 mM Hepes. Plate 5 days before the experiment and do not refresh media. At the point the experiment begins, the cells should be 80–90% confluent. Collect M1 cells in 50 ml tube and centrifuge 1000 rpm for 5 min. Resuspend the cell pellet in "quiescing medium" which is RPMI supplemented with Pen/Strep, glutamine. (It is important to note that quiescing medium contains neither serum nor growth factors.) Centrifuge again at 1000 rpm for 5 min to wash the cells. Again, resuspend the cells in quiescing medium. Incubate the M 1 cells in quiescing medium for 16 hours at 37° C.

Pre-warm quiescing medium (for M1 cells) and a metal tube rack to 37° C. Pre-cool quiescing media (for NIH-3T3 cells) and sterile Eppendorf tubes containing 0.5 ml of sample. Do not add proteins to warm media ahead of time so they will not degrade. Resuspend M1 cells to 5.0×10$^7$ cells per 0.5 ml quiescing media. Place all tubes on per warmed metal rack and leave at 37° C. until ready to begin. Add samples to these pre-aliquoted tubes. LIF is used as a positive control for CLC in these protein tyrosine phosphorylation studies. The preparation of M1 and NIH-3T3 cells differs slightly as follows:

For M1 cells: Mix 0.5 ml with pre-aliquoted samples to stimulate cells so total of 1 ml now. Immediately incubate at 37° C. for 5–7 min. Quickly centrifuge cells for 1 min. Aspirate media and add 1.0 ml cold lysis buffer plus additives [Lysis Buffer: 20 mM Tris pH 8.0,137 mM NaCl, 10% glycerol, 1% NP-40; Additives: leucine (1000×), EDTA (1000×), Naf (1000×), E64 (1000×), Aprotinin (1000×), sodium ortho-vanidate (100×), PMSF 0.1 mM final]. Rock the mixture at 4° C. for 15–30 min. Centrifuge 30 min 4° C. max speed.

For 3T3 cells: 15 Cm$^2$ plate 90% confluent, 2 plates per sample, and there are 5 samples. Aspirate to 7 ml conditioned media remain on cells. Add additives directly to 7 ml conditioned media on plates. Mix plates to stimulate cells. Immediately incubate at 37° C. for 5–7 min. Quickly dilute stimulating media by pouring off stimulating media and pouring on to plate generous amount of ice cold quiescing media. Pour off and repeat 3–4 times. Then, aspirate media and add 1.0 ml cold lysis buffer plus additives. Rock the mixture at 4° C. for 15–30 min. Centrifuge 30 min 4° C. max speed.

For both M1 and NIH-3T3 cells: carefully transfer 1 ml supernatant to new tube. Remove approximately 50 µl of lysate for use as a control on the gel. The remainder will be immunoprecipitated.

Incubate the lysate with approximately 50 µl anti-gp 130 antibody (dilute to 0.02 mg/ml with lysis buffer and protease inhibitors) at 4° C. overnight with rocking. The next day, add 50% protein-A sepharose slurry to each tube. Rock the tubes at 4° C. for 1 h. Following the incubation, remove 35 µl of the cell lysate and spin down (by virute of the sephaose beads) for 5 min at 700 rpm. Discard 0.9 ml of the supernatant while taking care to not disturb the pellet. Add 1 ml Lysis Buffer (without PMSF) and mix well by light shaking and inverting. Do not vortex or flick tubes. Centrifuge all tubes at 4° C. at a low speed for 5 min. Repeat washes for total of 2 times [Wash Buffer: 20 mM Tris pH 8.0, 137 mM NaCl, 10% glycerol, 1% NP-40]. Wash one time in 20 mM Tris pH 8.0, 300 mM NaCl, 10% glycerol, 1% NP-40. Finally, wash once in 20 mM Tris pH 8.0, 10% glycerol. Remove all wash buffer while taking great care to not lose any beads.

Electrophoretically separate the samples on a 10% polyacrylamide gel in a Tris-Glycine buffer. Electrotransfer the proteins in the gel to a nylon membrane in Western Transfer Buffer according to methods well-known in the art and then air dry the blots (membranes) [Western Transfer Buffer: 12 g Tris Base; 14.4 g glycine; 200 ml methanol; q.s. to 1L with water]. Wash the blots 2 times in 1×TBST for 5 min with shaking [10×TBST: 0.2 M Tris pH 8.0, 0.15 M NaCl, 0.5% Tween-20; dilute 1:10 with distilled H$_2$O to obtain 1×TBST]. Incubate 1 hour RT with shaking in a 2% blocking solution [Blocking Solution: 1 g dry milk, 50 ml 1×TBST]. Perform three separate rinses of the blocked blots with 1×TBST for 5 min.

Add primary antibody, anti-4G10 wash cover, and rock at 4° C. overnight in a solution of 1 µg/ml antibody in 1×TBST in a total volume of 30 ml. Remove the primary antibody. Wash with 1×TBST at room temperature (RT) for 10 min for a total of 3 washes. Add secondary antibody (in this case, a goat anti-mouse anti-phosphotyrosine conjugate at a 1:7500 dilution diluted in 1×TBST). Shake at RT for 1 h. Wash 4 times in 1×TBST with each wash for 5 min at RT.

Detect tyrosine phosphorylation by color change of the blot using color detection AP Buffer [AP Buffer: 4.5 ml 1 M Tris at pH 9.5, 0.225 ml 1M MgCl$_2$, 300 µl NBT, 150 µl BCIP, bring up to 45 ml with water for final concentrations of 100 mM Tris, pH 9.5, 5 mM MgCl$_2$]. Rock at RT until color change is background is low. Wash with sterile water for 1 hour at RT and air dry.

Results from phosphorylation experiments performed essentially as described above which were directed to a characterization of a functional role of CLC of the present invention are as follows. In an experiment in which M1 cells were treated with a CLC or a LIF supernatant, both CLC and LIF produced a band of phosphorylated protein with an apparent molecular mass of 32 kDa in extracts prepared from M1 cells indicating that one or more signal transduction pathways were activated in the cells and that tyrosine phosphorylation events characterized the activation of the pathway(s).

Example 6

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element (ISRE), located in the promoter of many genes. The binding of a protein to these elements alter the expression of the associated gene.

GAS and ISRE elements are recognized by a class of transcription factors called signal transducers and activators of transcription, or "STATs". There are six members of the STATs family. Stat 1 and Stat3 are present in many cell types, as is Stat2 (as voresponse to IFN-a is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below (adapted from review by Schidler and Darnell, *Ann. Rev. Biochem.* 64:621–51 (1995)). A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser, where Xxx represents any amino acid residue (SEQ ID NO:15)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway (see Table below). Thus, by using GAS elements linked to reporter molecules, activators of the Jaks-STATs pathway can be identified. Serum response elements (SREs) play a similar role in signal transduction although the DNA sequence which mediates a serum response is unique from the GAS or ISRE sequences.

| Ligand | JAKs tyk 2 | Jak 1 | Jak 2 | STATS Jak 3 | GAS or ISRE |
|---|---|---|---|---|---|
| IFN family | | | | | |
| IFN-a/b | + | + | – | – | 1,2,3 ISRE |
| IFN-g | | + | + | – | 1 GAS (IRF1>Lys6>IFP) |
| IL-10 | + | ? | ? | – | 1,3 |
| gp130 family | | | | | |
| IL-6 (Pleiotropic) | + + | + | ? | 1,3 | GAS (IRF1>Lys6>IFP) |
| IL-11 (Pleiotropic) | ? + | ? | ? | 1,3 | |
| OnM (Pleiotropic) | ? + | + | ? | 1,3 | |
| LIF (Pleiotropic) | ? + | + | ? | 1,3 | |
| CNTF (Pleiotropic) | –/+ + | + | ? | 1,3 | |
| G-CSF (Pleiotropic) | ? + | ? | ? | 1,3 | |
| IL-12 (Pleiotropic) | + – | + | + | 1,3 | |
| g-C family | | | | | |
| IL-2 (lymphocytes) | – + | – | + | 1,3,5 | GAS |
| IL-4 (lymph/myeloid) | – + | – | + | 6 | GAS |
| | | | | | (IRF1 = IFP>>Ly6)(IgH) |
| IL-7 (lymphocytes) | – + | – | + | 5 | GAS |
| IL-9 (lymphocytes) | – + | – | + | 5 | GAS |
| IL-13 (lymphocyte) | – + | ? | ? | 6 | GAS |
| IL-15 | ? | + | ? | + | 5 GAS |
| gp140 family | | | | | |
| IL-3 (myeloid) | – | – | + | – | 5 GAS |
| | | | | | (IRF1>IFP>>Ly6) |
| IL-5 (myeloid) | – | – | + | – | 5 GAS |
| GM-CSF (myeloid) | – | – | + | – | 5 GAS |
| Growth hormone family | | | | | |
| GH | ? | – | + | – | 5 |
| PRL | ? +/– | + | – | 1,3,5 | |
| EPO | ? | – | + | – | 5 |
| | | | | | GAS(B–CAS>IRF1=IFP>>Ly6) |
| Receptor Tyrosine Kinases | | | | | |
| EGF | ? | + | + | – | 1,3 GAS(IRF1) |
| PDGF | ? | + | + | – | 1,3 |
| CSF-1 | ? | + | + | – | 1,3 GAS (not IRF1) |

To construct a synthetic GAS containing promoter element, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman, et al., *Immunity* 1:457–468 (1994)), although other GAS or ISRE elements can be used instead. The 5' primer also contains 18 bp of sequence complementary to the SV40 early promoter sequence and is flanked with an Xho I site. The sequence of the 5' primer is: 5'-GCG CCT CGA GAT TTC CCC GAA ATC TAG ATT TCC CCG AAA TGA TTT CCC CGA AAT GAT TTC CCC GAA ATA TCT GCC ATC TCA ATT AG-3' (SEQ ID NO:16). The downstream primer is complementary to the SV40 promoter and is flanked with a Hin dIII site. The sequence of the 3' primer is: 5'-GCG GCA AGC TTT TTG CAA AGC CTA GGC-3'(SEQ ID NO:17).

PCR amplification is performed using the SV40 promoter template present in the b-gal:promoter plasmid obtained from Clontech. The resulting PCR fragment is digested with Xho I and Hin dIII and subcloned into BLSK2- (Stratagene). Sequencing with forward and reverse primers confirms that the insert contains the following sequence: 5'-CTC GAG ATT TCC CCG AAA TCT AGA TTT CCC CGA AAT GAT TTC CCC GAA ATG ATT TCC CCG AAA TAT CTG CCA TCT CAA TTA GTC AGC AAC CAT AGT CCC GCC CCT AAC TCC GCC CAT CCC GCC CCT AAC TCC GCC CAG TTC CGC CCA TTC TCC GCC CCA TGG CTG ACT AAT TTT TTT TAT TTA TGC AGA GGC CGA GGC CGC CTC GGC CTC TGA GCT ATT CCA GAA GTA GTG AGG AGG CTT TTT TGG AGG CCT AGG CTT TTG CAA AAA GCT T-3' (SEQ ID NO:18).

With this GAS promoter element linked to the SV40 promoter, a GAS:SEAP2 reporter construct is next engineered. Here, the reporter molecule is a secreted alkaline phosphatase, or "SEAP". Clearly, however, any reporter molecule can be instead of SEAP, in this or in any of the other Examples. Well-known reporter molecules that can be used instead of SEAP include chloramphenicol acetyltransferase (CAT), luciferase, alkaline phosphatase, b-galactosidase, green fluorescent protein (GFP), or any protein detectable by an antibody.

The above sequence confirmed synthetic GAS-SV40 promoter element is subcloned into the pSEAP-Promoter vector obtained from Clontech using Hin dIII and Xho I, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using Sal I and Not I, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding.

Other constructs can be made using the above description and replacing GAS with a different promoter sequence. For example, construction of reporter molecules containing NF-kB and EGR promoter sequences are described in Examples 6 and 8. However, many other promoters can be substituted using the protocols described in these Examples. For instance, SRE, IL-2, NFAT, or Osteocalcin promoters can be substituted, alone or in combination (e.g., GAS/NF-kB/EGR, GAS/NF-kB, Il-2/NFAT, or NF-kB/GAS). Similarly, other cell lines can be used to test reporter construct activity, such as HeLa (epithelial), HUVEC (endothelial), Reh (B-cell), Saos-2 (osteoblast), HUVAC (aortic) or cardiomyocyte.

Example 7

Screening Assay for T-cell Activity

The following protocol is used to assess T-cell activity of CLC by determining whether CLC supernatant proliferates and/or differentiates T-cells. T-cell activity is assessed using the GAS/SEAP/Neo construct produced in Example 6. Thus, factors that increase SEAP activity indicate the ability to activate the Jaks-STATs signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th 1 helper cells. In order to generate stable cell lines, approximately 2 million Jurkat cells are transfected with the GAS-SEAP/neo vector using DMRIE-C (Life Technologies; transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 μl of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 μg of plasmid DNA in a T25 flask. Add 2.5 ml OPTI-MEM containing 50 μl of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing CLC polypeptides or CLC induced polypeptides.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 μl of cells into each well (therefore adding 100,000 cells per well).

After all the plates have been seeded, 50 μl of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 μl samples from each well are then transferred to an opaque 96 well plate using a 12 channel pipette. The opaque plates should be covered (using sellophene covers) and stored at −20° C. until SEAP assays are performed according to Example 10. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30-fold induction is typically observed in the positive control wells.

Example 7

Assay Identifying Myeloid Activity

The following protocol is used to assess myeloid activity of CLC by determining whether CLC proliferates and/or differentiates myeloid cells. Myeloid cell activity is assessed using the GAS/SEAP/Neo construct produced in Example 6. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 6, a DEAE-Dextran method (Kharbanda, et. al., *Cell Growth & Differentiation* 5:259–265 (1994)) is used. First, harvest $2 \times 10^7$ U937 cells and wash with PBS. The U937 cells are usually grown in RPMI 1640 medium containing 10% heat-inactivated fetal bovine serum (FBS) supplemented with 100 units/mil penicillin and 100 mg/ml streptomycin.

Next, suspend the cells in 1 ml of 20 mM Tris-HCl (pH 7.4) buffer containing 0.5 mg/ml DEAE-Dextran, 8 $\mu$g GAS-SEAP2 plasmid DNA, 140 mM NaCl, 5 mM KCl, 375 $\mu$M $Na_2HPO_47H_2O$, 1 mM $MgCl_2$, and 675 $\mu$M $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 $\mu$g/ml G418. The G418-free medium is used for routine growth but every one to two months, the cells should be re-grown in 400 $\mu$g/ml G418 for couple of passages.

These cells are tested by harvesting $1 \times 10_8$ cells (this is enough for ten 96-well plates assay) and wash with PBS. Suspend the cells in 200 ml above described growth medium, with a final density of $5 \times 10^5$ cells/ml. Plate 200 $\mu$l cells per well in the 96-well plate (or $1 \times 10^5$ cells/well).

Add 50 $\mu$l of a CLC supernatant and incubate at 37° C. for 48 to 72 hr. As a positive control, 100 Unit/ml interferon gamma can be used which is known to activate U937 cells. Over 30-fold induction is typically observed in the positive control wells. SEAP assay the supernatant according to the protocol described in Example 10.

Example 8

Screening Assay for the Identification of Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by CTGF-4.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by CLC can be assessed.

The EGR/SEAP reporter construct can be assembled by the following protocol. The EGR-1 promoter sequence (−633 to +1; Sakamoto, K., et al., *Oncogene* 6:867–871 (1991)) can be PCR amplified from human genomic DNA using the following primers. The 5' primer has the sequence: 5'-GCG CTC GAG GGA TGA CAG CGA TAG AAC CCC GG-3' (SEQ ID NO:19) and the 3' primer has the sequence: 5'-GCG AAG CTT CGC GAC TCC CCG GAT CCG CCT C-3' (SEQ ID NO:20).

Using the GAS:SEAP/Neo vector produced in Example 6, EGR1 amplified product can then be inserted into this vector. Linearize the GAS:SEAP/Neo vector using restriction enzymes Xho I and Hin dIII, removing the GAS/SV40 stuffer. Restrict the EGR1 amplified product with these same enzymes. Ligate the vector and the EGR1 promoter.

To prepare 96 well-plates for cell culture, two ml of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 $\mu$g/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 cell cultures. EGR-SEAP/PC12 stable cells are obtained by growing the cells in 300 $\mu$g/ml G418. The G418-free medium is used for routine growth but every one to two months, the cells should be re-grown in 300 $\mu$g/ml G418 for several passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 $\mu$l of the cell suspension to each well of 96-well plate (equivalent to $1 \times 10^5$ cells/well). Add 50 $\mu$l of a CLC supernatant and incubate at 37° C. for 48 to 72 hr. As a positive control, a growth factor known to activate PC12 cells through EGR can be used, such as 50 $\mu$g/ul of neuronal growth factor (NGF). Over fifty-fold induction of SEAP is typically seen in the positive control wells. SEAP assay the supernatant according to Example 10.

Example 9

Screening Assay for NF-kB Activity

NF-kB (Nuclear Factor-kB) is a transcription factor activated by a wide variety of agents including the inflammatory cytokines IL-1 and TNF, CD30 and CD40, lymphotoxin-a and lymphotoxin-b, by exposure to LPS or thrombin, and by expression of certain viral gene products. As a transcription factor, NF-kB regulates the expression of genes involved in immune cell activation, control of apoptosis (NF-kB appears to shield cells from apoptosis), B- and T-cell development, anti-viral and antimicrobial responses, and multiple stress responses.

In non-stimulated conditions, NF-kB is retained in the cytoplasm with I-kB (Inhibitor-kB). However, upon stimulation, I-kB is phosphorylated and degraded, causing NF-kB to shuttle to the nucleus, thereby activating transcription of target genes. Target genes activated by NF-kB include IL-2, IL-6, GM-CSF, ICAM- 1 and class 1 MHC.

Due to its central role and ability to respond to a range of stimuli, reporter constructs utilizing the NF-kB promoter element are used to screen the supernatants produced in Example 6. Activators or inhibitors of NF-kB would be useful in treating diseases. For example, inhibitors of NF-kB could be used to treat those diseases related to the acute or chronic activation of NF-kB, such as rheumatoid arthritis and others.

To construct a vector containing the NF-kB promoter element, a PCR based strategy is employed. The 5' primer contains four tandem copies of the NF-kB binding site (5'-GGG GAC TTT CCC-3'; SEQ ID NO:21), 18 bp of sequence complementary to the 5' end of the SV40 early promoter sequence, and is flanked with an Xho I site and has the following sequence: 5'-GCG GCC TCG AGG GGA CTT TCC CGG GGA CTT TCC GGG GAC TTT CCG GGA CTT TCC ATC CTG CCA TCT CAA TTA G-3' (SEQ ID NO:22). The 3' primer is complementary to the 3' end of the SV40 promoter, is flanked with a Hin dIII site and has the following sequence: 5'-GCG GCA AGC TTT TTG CAA AGC CTA GGC-3' (SEQ ID NO:23).

PCR amplification is performed using the SV40 promoter template present in the pb-gal:promoter plasmid obtained from Clontech. The resulting PCR fragment is digested with Xho I and Hin dIII and subcloned into BLSK2-(Stratagene).

Sequencing with the T7 and T3 primers confirms the insert contains the following sequence: 5'-CTC GAG GGG ACT TTC CCG GGG ACT TTC CGG GGA CTT TCC GGG ACT TTC CAT CTG CCA TCT CAA TTA GTC AGC AAC CAT AGT CCC GCC CCT AAC TCC GCC CAT CCC GCC CCT AAC TCC GCC CAG TTC CGC CCA TTC TCC GCC CCA TGG CTG ACT AAT TTT TTT TAT TTA TGC AGA GGC CGA GGC CGC CTC GGC CTC TGA GCT ATT CCA GAA GTA GTG AGG AGG CTT TTT TGG AGG CCT AGG CTT TTG CAA AAA GCT T-3' (SEQ ID NO:24).

Next, replace the SV40 minimal promoter element present in the pSEAP2-promoter plasmid (Clontech) with this NF-kB/SV40 fragment using Xho I and Hin dIII. However, this vector does not contain a neomycin resistance gene, and therefore, is not preferred for mammalian expression systems.

In order to generate stable mammalian cell lines, the NF-kB/SV40/SEAP cassette is removed from the above NF-kB/SEAP vector using restriction enzymes Sal I and Not I, and inserted into a vector containing neomycin resistance. Particularly, the NF-kB/SV40/SEAP cassette was inserted into pGFP-1 (Clontech), replacing the GFP gene, after restricting pGFP-1 with Sal I and Not I.

Once NF-kB/SV40/SEAP/Neo vector is created, stable Jurkat T-cells are created and maintained according to the protocol described in Example 9. Similarly, the method for assaying supernatants with these stable Jurkat T-cells is also described in Example 9. As a positive control, exogenous TNF alpha (0.1,1, 10 ng) is added to wells H9, H10, and H11, with a 5–10 fold activation typically observed.

Example 10

Assay for SEAP Activity

As a reporter molecule for the assays described in Examples 6–9, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 $\mu$l of 2.5×dilution buffer into Optiplates containing 35 $\mu$l of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 $\mu$l Assay Buffer and incubate at room temperature 5 min. Empty the dispenser and prime with an appropriate amount of Reaction Buffer. Add 50 $\mu$l Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later. Read the relative light unit in the luminometer. Set H12 as blank, and print the results. An increase in chemiluminescence indicates reporter activity.

Results of experiments analyzing the involvement of the SRE and GAS signaling pathways using an SEAP reporter approach indicated that supernatants from 293T cells transfected with the CLC mammalian expression vector described in Example 3(b) resulted in an activation of the SRE element in TF-1 cells of 2.6-fold over the negative control level. The same experiment was repeated replacing TF-1 cells with M1 cells and a 3.2-fold induction of the GAS element was observed. In analogous experiments designed to analyze activity of a GAS/SEAP construct in TF-1 cells in response to treatment with supernatants obtained from 293T cells transfected with the same CLC expression construct, a 4.6-fold activation of the GAS element was observed. The same experiment was repeated replacing TF-1 cells with M1 cells and a 4.5-fold induction of the GAS element was observed. Thus, signal transduction pathways involving the GAS and SRE elements as described above are activated in TF-1 and M1 cells in response to CLC stimulation.

Example 11

Effect of CLC on Cellular Proliferation.

The effect of CLC on cellular proliferation can be assayed in M1 cells by BrdU incorporation. $1\times10^4$ cells/100 $\mu$L are dispensed into 96-well cell culture plates and labeled with 10 $\mu$L BrdU. CLC is added to the cells at several doses (0, 5, 25, and 100 $\mu$L) and LIF is added to the cells as a positive control at a dose of 100 $\mu$L. The cells are allowed to grow for 72 hours at 37° C. The amount of BrdU incorporation is determined by the Cell Proliferation ELISA BrdU colorimetric kit (Boehringer Mannheim).

CLC and LIF inhibited MI cell proliferation at a dose of 100 $\mu$L at levels of 3.1-fold and 4.8-fold, respectively, with respect to the negative control. Treatment of the cells with CLC concentrations of 0, 5, and 25 $\mu$L each had a similar lack of response.

Example 12

Effect of CLC on Cardiac Myocyte Hypertrophy.

Primary cardiomyocytes, primary neuronal cultures, or other cells are plated at a low density and cultured using standard culturing techniques. Cultures are treated with 1% BSA or mock-treated as negative controls, phenylephrine as a positive control, or with supernatants from 293T cells transfected with the CLC mammalian expression construct described in Example 3(b). Cultures are evaluated at a point between 48 and 72 hours post-treatment by counting the number of cells in four non-overlapping fields in three independent cultures and averaging the results.

The mock-transfected 293T cell culture supernatant possesses a cardiomyocyte hypertrophic activity. Cultures transfected with CLC reduce this activity by 2-fold. Further, there is a clear increase of the sympathetic neuron counts in samples treated with CLC-transfected supernatants, an activity common to IL-6 family members. Results are shown in the following table.

| Culture Condition | No. Active Myocytes | No. Neurons |
| --- | --- | --- |
| 1% BSA | 36 | 22 |
| Mock transfected | 105 | 26 |
| Phenylephrine | 92 | 28 |
| CLC-transfected | 50 | 86 |

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule consisting of a polynucleotide which encodes the CLC polypeptide shown as residues 3 to 198 of SEQ ID NO:2.

2. An isolated nucleic acid molecule comprising a polynucleotide having the complete nucleotide sequence in FIGS. 1A and 1B (SEQ ID NO:1).

3. An isolated nucleic acid molecule comprising a polynucleotide having the nucleotide sequence in FIGS. 1A and 1B (SEQ ID NO:1) encoding the CLC polypeptide having the amino acid sequence in positions −27 to 198 of SEQ ID NO:2.

4. An isolated nucleic acid molecule comprising a polynucleotide having the nucleotide sequence in FIGS. 1A and 1B (SEQ ID NO:1) encoding the CLC polypeptide having the amino acid sequence in positions −26 to 198 of SEQ ID NO:2.

5. An isolated nucleic acid molecule comprising a polynucleotide having the nucleotide sequence in FIGS. 1A and 1B (SEQ ID NO:1) encoding the mature CLC polypeptide having the amino acid sequence from about 1 to about 198 in SEQ ID NO:2.

* * * * *